US012718909B2

(12) United States Patent
Li et al.

(10) Patent No.: US 12,718,909 B2
(45) Date of Patent: Aug. 25, 2026

(54) PROPERTY MODEL TRAINING METHOD AND APPARATUS, ELECTRONIC DEVICE, COMPUTER-READABLE STORAGE MEDIUM, AND COMPUTER PROGRAM PRODUCT

(71) Applicant: Tencent Technology (Shenzhen) Company Limited, Shenzhen (CN)

(72) Inventors: Lanqing Li, Shenzhen (CN); Liang Zeng, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 384 days.

(21) Appl. No.: 18/599,068

(22) Filed: Mar. 7, 2024

(65) Prior Publication Data

US 2024/0212798 A1 Jun. 27, 2024

Related U.S. Application Data

(63) Continuation of application No. PCT/CN2023/109150, filed on Jul. 25, 2023.

(30) Foreign Application Priority Data

Sep. 1, 2022 (CN) ......................... 202211067742.7

(51) Int. Cl.
*G16C 20/70* (2019.01)
*G16C 20/30* (2019.01)

(52) U.S. Cl.
CPC ............. *G16C 20/70* (2019.02); *G16C 20/30* (2019.02)

(58) Field of Classification Search
CPC ........ G16C 20/70; G16C 20/30; G16C 20/10; G16C 20/20; G06N 3/0464; G06N 3/045;
(Continued)

(56) References Cited

U.S. PATENT DOCUMENTS

2016/0196323 A1* 7/2016 Kim ........................ G16C 20/10 707/737
2020/0176087 A1* 6/2020 Colby .................... G06N 3/088
(Continued)

FOREIGN PATENT DOCUMENTS

CN 110634539 A 12/2019
CN 111755078 A 10/2020
CN 112634992 A 4/2021

OTHER PUBLICATIONS

Tencent Technology, WO+IPRP, PCT/CN2023/109150, Mar. 1, 2025, 6 pgs.

(Continued)

*Primary Examiner* — Mohammad K Islam
(74) *Attorney, Agent, or Firm* — Morgan, Lewis & Bockius LLP

(57) ABSTRACT

This application provides a molecular property model training method performed by an electronic device. The method includes: obtaining a plurality of pieces of first sample data associated with a plurality of chemical reactions; performing forward propagation on a plurality of pieces of first molecule data of the plurality of pieces of first sample data in a first encoding network to obtain a first encoding feature of each first molecule data; determining an uncertainty loss of the plurality of chemical reactions based on the first encoding features of the plurality of pieces of first molecule data of the plurality of pieces of first sample data and indicator data of each chemical reaction; performing backward propagation processing on the uncertainty loss in the first encoding network to obtain an updated first encoding network as a molecular property model, the molecular property model being used for determining a property of a target molecule.

20 Claims, 7 Drawing Sheets

(58) Field of Classification Search
CPC ...... G06N 3/0495; G06N 3/082; G06N 3/084; G06F 18/25; Y02P 90/30
See application file for complete search history.

(56) References Cited

U.S. PATENT DOCUMENTS

| | | | | |
|---|---|---|---|---|
| 2021/0217497 | A1 | 7/2021 | Hou et al. | |
| 2022/0067940 | A1* | 3/2022 | Heng | G06N 3/0464 |
| 2022/0383994 | A1* | 12/2022 | Rabideau | G06N 3/0455 |
| 2022/0406412 | A1* | 12/2022 | Segler | G16C 20/10 |
| 2023/0081412 | A1* | 3/2023 | Fu | G16C 20/70<br>702/27 |

OTHER PUBLICATIONS

Tencent Technology, Extended European Search Report, EP Patent Application No. 23855807.6, Apr. 28, 2025, 6 pgs.
Hongwei Wang et al., "Chemical-Reaction-Aware Molecule Representation Learning", ARXIV.org, Computer Science > Machine Learning, Sep. 2021, 18 pgs.
Johan Broberg et al., "Pre-Training Transformers for Molecular Property Prediction Using Reaction Prediction", ARXIV.org, Computer Science > Machine Learning, Jul. 2022, 8 pgs.
Yuyang Wang et al., "Molecular Contrastive Learning of Representations Via Graph Neural Networks", Nature Machine Intelligence, vol. 4, No. 3, Mar. 2022, 9 pgs.
Tencent Technology, ISR, PCT/CN2023/109150, Nov. 11, 2023, 2 pgs.

* cited by examiner

PROPERTY MODEL TRAINING METHOD AND APPARATUS, ELECTRONIC DEVICE, COMPUTER-READABLE STORAGE MEDIUM, AND COMPUTER PROGRAM PRODUCT

CROSS-REFERENCE TO RELATED APPLICATIONS

This application is a continuation application of PCT Patent Application No. PCT/CN2023/109150, entitled "PROPERTY MODEL TRAINING METHOD AND APPARATUS, ELECTRONIC DEVICE, COMPUTER-READABLE STORAGE MEDIUM, AND COMPUTER PROGRAM PRODUCT" filed on Jul. 25, 2023, which is based on and claims priority to Chinese Patent Application No. 202211067742.7, entitled "PROPERTY MODEL TRAINING METHOD AND APPARATUS, ELECTRONIC DEVICE, COMPUTER-READABLE STORAGE MEDIUM, AND COMPUTER PROGRAM PRODUCT" filed on Sep. 1, 2022, all of which is incorporated herein by reference in its entirety.

FIELD OF THE TECHNOLOGY

This application relates to the field of artificial intelligence technologies, and in particular, to a molecular property model training method and apparatus, an electronic device, a computer-readable storage medium, and a computer program product.

BACKGROUND OF THE DISCLOSURE

Artificial intelligence (AI) is a comprehensive technology of computer science to study design principles and implementation methods of various intelligent machines, to enable the machines to have functions of perception, reasoning, and decision-making. The artificial intelligence technology is a comprehensive subject that relates to a wide range of fields, such as a natural language processing technology and machine learning/deep learning. With the development of technologies, the artificial intelligence technology will be applied to more fields and play an increasingly important role.

A molecular property prediction task is of extremely important significance to the field of computational chemistries and pharmaceuticals. In related art, molecular representations are usually determined based on a template matching method. However, there are many types of molecules, and it is difficult for molecular templates to cover a large number of molecules to be searched. In related art, a data-driven method is also used to obtain the molecular representations. However, due to limitation of sparse labeled molecule data, a training effect of a molecular property model is poor, resulting in low property prediction accuracy of the molecular property model.

SUMMARY

Embodiments of this application provide a molecular property model training method and apparatus, an electronic device, a computer-readable storage medium, and a computer program product, which can improve a training effect of the molecular property model, thereby improving prediction accuracy of the molecular property model.

The technical solutions of the embodiments of this application are implemented as follows:

An embodiment of this application provides a molecular property model training method. The method is executed by an electronic device and includes:

obtaining a plurality of pieces of first sample data associated with a plurality of chemical reactions, each first sample data including a plurality of pieces of first molecule data related to a chemical reaction and indicator data of the chemical reaction;

performing forward propagation on the plurality of pieces of first molecule data of the plurality of pieces of first sample data in a first encoding network to obtain a first encoding feature of each first molecule data;

determining an uncertainty loss of the plurality of chemical reactions based on the first encoding features of the plurality of pieces of first molecule data of the plurality of pieces of first sample data and indicator data of each chemical reaction, the uncertainty loss being used for fitting uncertainty of establishment of the plurality of chemical reactions; and performing backward propagation processing on the uncertainty loss in the first encoding network to obtain an updated first encoding network as a molecular property model, the molecular property model being used for determining a property of a target molecule.

An embodiment of this application provides an electronic device, including:

a memory, configured to store computer executable instructions; and a processor, configured to execute the computer executable instructions stored in the memory to implement the molecular property model training method according to the embodiments of this application.

An embodiment of this application provides a non-transitory computer-readable storage medium, having computer executable instructions stored thereon, the computer executable instructions being configured to, when executed by a processor, implement the molecular property model training method according to the embodiments of this application.

The embodiments of this application have the following beneficial effects:

In the embodiments of this application, the first encoding network is first pre-trained, and then the molecular property model is trained based on a pre-trained first encoding network. In a pre-training process, the pre-training process is supervised based on a chemical reaction relationship and the indicator data of the chemical reaction, and the indicator data of the chemical reaction is used to model the uncertainty of establishment of the chemical reactions, so that a molecular representation capability of the first encoding network can be effectively improved. Therefore, the molecular property model is trained based on the first encoding network. This can effectively improve a training effect of the molecular property model, thereby improving prediction accuracy of the molecular property model.

DESCRIPTION OF EMBODIMENTS

Figure 1:
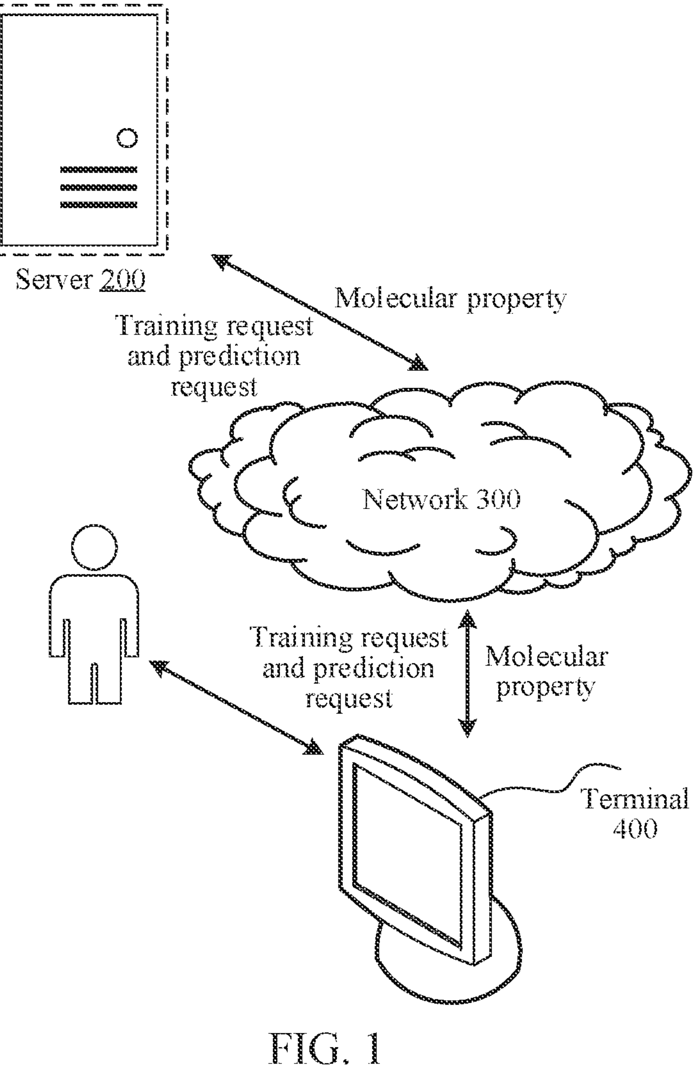
FIG. 1 is a schematic diagram of a structure of a molecular property model training system according to an embodiment of this application.

To make the objectives, technical solutions, and advantages of this application clearer, the following describes this application in further detail with reference to the accompanying drawings. The described embodiments are not to be considered as a limitation to this application. All other embodiments obtained by a person of ordinary skill in the art without creative efforts fall within the protection scope of this application.

In the following description, "some embodiments" are involved, which describe a subset of all possible embodiments, but it may be understood that "some embodiments" may be the same subset or different subsets of all the possible embodiments, and may be combined with each other without conflict.

In the following description, the term "first/second/third" involved is only used for distinguishing similar objects and does not represent a specific order of objects. Understandably, "first/second/third" may be interchanged with a specific order or priority if permitted, so that embodiments of this application described here may be implemented in an order other than that illustrated or described here.

Unless otherwise defined, meanings of all technical and scientific terms used in this specification are the same as those usually understood by a person skilled in the art to which this application belongs. The terms used herein are only used for describing the purpose of embodiments of this application, not intended to limit this application.

Before the embodiments of this application are further described in detail, a description is made on terms in the embodiments of this application, and the terms in the embodiments of this application are applicable to the following explanations.

(1) Molecular representation: Molecular representation learning aims to embed molecules into vector space. An encoding feature of the vector space may be used to represent property information of the molecules in a molecule-related learning task, so as to perform a prediction task based on the molecular representation, for example, to predict a molecule property.

(2) Chemical reaction: It is a process in which molecules break up into atoms, and the atoms are rearranged to form new molecules. A reaction is often accompanied by luminescence, heat generation, color change, formation of precipitates, and the like. A basis for determining whether a reaction is a chemical reaction is whether new molecules are generated in the reaction.

(3) Graph neural network: It is a general term for algorithms that use a neural network to learn molecule graph data, extract and explore features and patterns in the molecule graph data and that meet requirements of a graph learning task, such as clustering, classification, prediction, segmentation, and generation.

(4) Chemical reaction yield: It is a ratio of a mass of an actual product to a mass of a theoretical product. For example, if 100 grams of a product may be theoretically obtained, but only 75 grams are actually obtained, a yield is 75/100*100%75%. Due to a loss in an actual production process, the yield definitely is less than 100%.

(5) Knowledge distillation: It is to transfer a learning behavior of a complex model to a learning behavior of a lightweight model. Output generated by the complex model is used as a soft target for training the lightweight model to guide training of the lightweight model and implement knowledge transfer.

The technical solutions for learning molecular representation in related art are mainly divided into three main categories: molecular fingerprint representation, string representation based on a simplified molecular input line entry system (SMILES), and graph representation based on molecules. A molecular property prediction task may be executed based on the foregoing molecular representations.

The molecular fingerprint representation is a typical molecular representation method which uses a molecular kernel function to generate continuous numerical representations. The SMILES-based character string can uniquely represent molecules according to a preset rule. The graph representation of the molecules can better express a two-dimensional topological structure of the molecules. Topological link relationships between different atoms in the molecules can be better captured by using a graph neural network technology to encode a molecule graph.

In related art, information related to chemical reactions is not integrated. For example, a yield of a chemical reaction is an important indicator to measure importance of the chemical reaction. A lack of such information greatly limits a prediction capability of the molecular property model. A chemical reaction data set does not include by-product free data, and the data set often includes loud noise, resulting in a lack of modeling of chemical reaction uncertainty in related art. There is an essential difference between tasks corresponding to a chemical reaction data set and a molecular property prediction data set. Therefore, it is necessary to transfer knowledges of a pre-trained chemical reaction data set to a downstream molecular property prediction data set.

To resolve the foregoing problems, embodiments of this application provide a molecular property model training method and apparatus, an electronic device, a computer-readable storage medium, and a computer program product, which can improve both accuracy and a speed of molecular energy computing.

The molecular property model training method according to the embodiments of this application may be independently implemented by a terminal/server, or may be implemented collaboratively by a terminal and a server. For example, the terminal is independently responsible for the molecular property model training method below. Alternatively, the terminal sends a training request for the molecular property model to the server, and the server executes the molecular property model training method based on the received training request. The server obtains a plurality of pieces of first sample data in one-to-one correspondence with a plurality of chemical reactions, where each first sample data includes a plurality of pieces of first molecule data related to a chemical reactions and indicator data of the chemical reaction; performs forward propagation on the plurality of pieces of first molecule data of the plurality of pieces of first sample data in a first encoding network to obtain a first encoding feature of each first molecule data; determines an uncertainty loss of the plurality of chemical reactions based on the first encoding features of the plurality of pieces of first molecule data of the plurality of pieces of first sample data and indicator data of each chemical reaction, and performs backward propagation processing on the uncertainty loss in the first encoding network to obtain an updated first encoding network; and trains a molecular property model based on the updated first encoding network to obtain a trained molecular property model. The server returns a training completion message. The terminal sends a property prediction request for a target molecule to the server, and the server predicts, based on the received property prediction request, a property of the target molecule by calling the molecular property model. In this way, research and development personnel can perform subsequent analysis and research based on the property of the target molecule.

The electronic device provided in the embodiments of this application for executing the molecular property model training method may be various types of terminal devices or servers. The server may be an independent physical server, a server cluster or distributed system including a plurality of physical servers, or a cloud server that provides cloud computing services. The terminal may be a smartphone, a tablet computer, a notebook computer, a desktop computer, a smart speaker, a smartwatch, or the like, but is not limited thereto. The terminal may be directly or indirectly connected to the server in a wired or wireless communication manner, which is not limited in this application.

A server is used as an example. For example, the server may be a server cluster deployed in a cloud and open artificial intelligence as a service (AIaaS) to users. An AIaaS platform splits some common types of AI services and provides independent or packaged services in the cloud. Such a service mode is similar to an AI-theme mall. All users can access one or more artificial intelligence services provided by the AIaaS platform via application programming interfaces.

For example, one of the artificial intelligence as a service may be a molecular property model training service. In other words, a molecular property model training program provided in the embodiments of this application is packaged in a server in the cloud. A user calls the molecular property model training service in the cloud service by using the terminal (on which a client runs, such as a compound screening client), so that the server deployed in the cloud calls the packaged molecular property model training program. The server obtains a plurality of pieces of first sample data in one-to-one correspondence with a plurality of chemical reactions, where each first sample data includes a plurality of pieces of first molecule data related to a chemical reaction and indicator data of the chemical reaction; performs forward propagation on the plurality of pieces of first molecule data of the plurality of pieces of first sample data in a first encoding network to obtain a first encoding feature of each first molecule data; determines an uncertainty loss of the plurality of chemical reactions based on the first encoding features of the plurality of pieces of first molecule data of the plurality of pieces of first sample data and indicator data of each chemical reaction, and performs backward propagation processing on the uncertainty loss in the first encoding network to obtain an updated first encoding network; and trains a molecular property model based on the updated first encoding network to obtain a trained molecular property model, and predicts a property of the target molecule by calling the molecular property model. In this way, research and development personnel can perform subsequent analysis and research based on the property of the target molecule.

FIG. 1 is a schematic diagram of an architecture of a molecular property model training system according to an embodiment of this application. A terminal 400 is connected to a server 200 via a network 300. The network 300 may be a wide area network, a local area network, or a combination of the two.

The terminal 400 (on which a client, such as a compound screening client, runs) may be used to obtain a training request for a molecular property model. For example, research and development personnel input a molecular property prediction task on an input interface of the terminal 400, and the training request for the molecular property model is automatically generated. The terminal 400 sends the training request for the molecular property model to the server 200. The server 200 obtains a plurality of pieces of first sample data in one-to-one correspondence with a plurality of chemical reactions, where each first sample data includes a plurality of pieces of first molecule data related to a chemical reaction and indicator data of the chemical reaction; performs forward propagation on the plurality of pieces of first molecule data of the plurality of pieces of first sample data in a first encoding network to obtain a first encoding feature of each first molecule data; determines an uncertainty loss of the plurality of chemical reactions based on the first encoding features of the plurality of pieces of first molecule data of the plurality of pieces of first sample data and indicator data of each chemical reaction, and performs backward propagation processing on the uncertainty loss in the first encoding network to obtain an updated first encoding network; and trains the molecular property model based on the updated first encoding network to obtain a trained molecular property model. The server 200 returns the molecular property model to the terminal 400. The research and development personnel input a target molecule on the input interface of the terminal 400, and the terminal predicts a property of the target molecule by calling the molecular property model. In this way, the research and development personnel can perform subsequent analysis and research based on the property of the target molecule.

In some embodiments, a molecule processing plug-in may be embedded in the client running on the terminal to implement the molecular property model training method locally on the client. For example, after obtaining the training request for the molecular property model, the terminal 400 calls the molecule processing plug-in to implement the molecular property model training method. The method includes: obtaining a plurality of pieces of first sample data in one-to-one correspondence with a plurality of chemical reactions, each first sample data including a plurality of pieces of first molecule data related to a chemical reaction and indicator data of the chemical reaction; performs forward propagation on the plurality of pieces of first molecule data of the plurality of pieces of first sample data in a first encoding network to obtain a first encoding feature of each first molecule data; determines an uncertainty loss of the plurality of chemical reactions based on the first encoding features of the plurality of pieces of first molecule data of the plurality of pieces of first sample data and indicator data of each chemical reaction, and performs backward propagation processing on the uncertainty loss in the first encoding network to obtain an updated first encoding network; and trains the molecular property model based on the updated first encoding network to obtain a trained molecular property model. The research and development personnel input a target molecule on the input interface of the terminal 400, and the terminal predicts a property of the target molecule by calling the molecular property model. In this way, the research and development personnel can perform subsequent analysis and research based on the property of the target molecule.

In some embodiments, after obtaining the training request for the molecular property model, the terminal 400 calls a molecule processing interface (which may be provided as a cloud service, that is, a molecule processing service) of the server 200. The server 200 obtains a plurality of pieces of first sample data in one-to-one correspondence with a plurality of chemical reactions, where each first sample data includes a plurality of pieces of first molecule data related to a chemical reaction and indicator data of the chemical reaction; performs forward propagation on the plurality of pieces of first molecule data of the plurality of pieces of first sample data in a first encoding network to obtain a first encoding feature of each first molecule data; determines an uncertainty loss of the plurality of chemical reactions based on the first encoding features of the plurality of pieces of first molecule data of the plurality of pieces of first sample data and indicator data of each chemical reaction, and performs backward propagation processing on the uncertainty loss in the first encoding network to obtain an updated first encoding network; and trains the molecular property model based on the updated first encoding network to obtain a trained molecular property model. The research and development personnel input a target molecule on the input interface of the terminal 400, the terminal calls the molecule processing interface of the server 200, and the server 200 predicts a property of the target molecule by calling the molecular property model. In this way, the research and development personnel can perform subsequent analysis and research based on the property of the target molecule.

Figure 2:
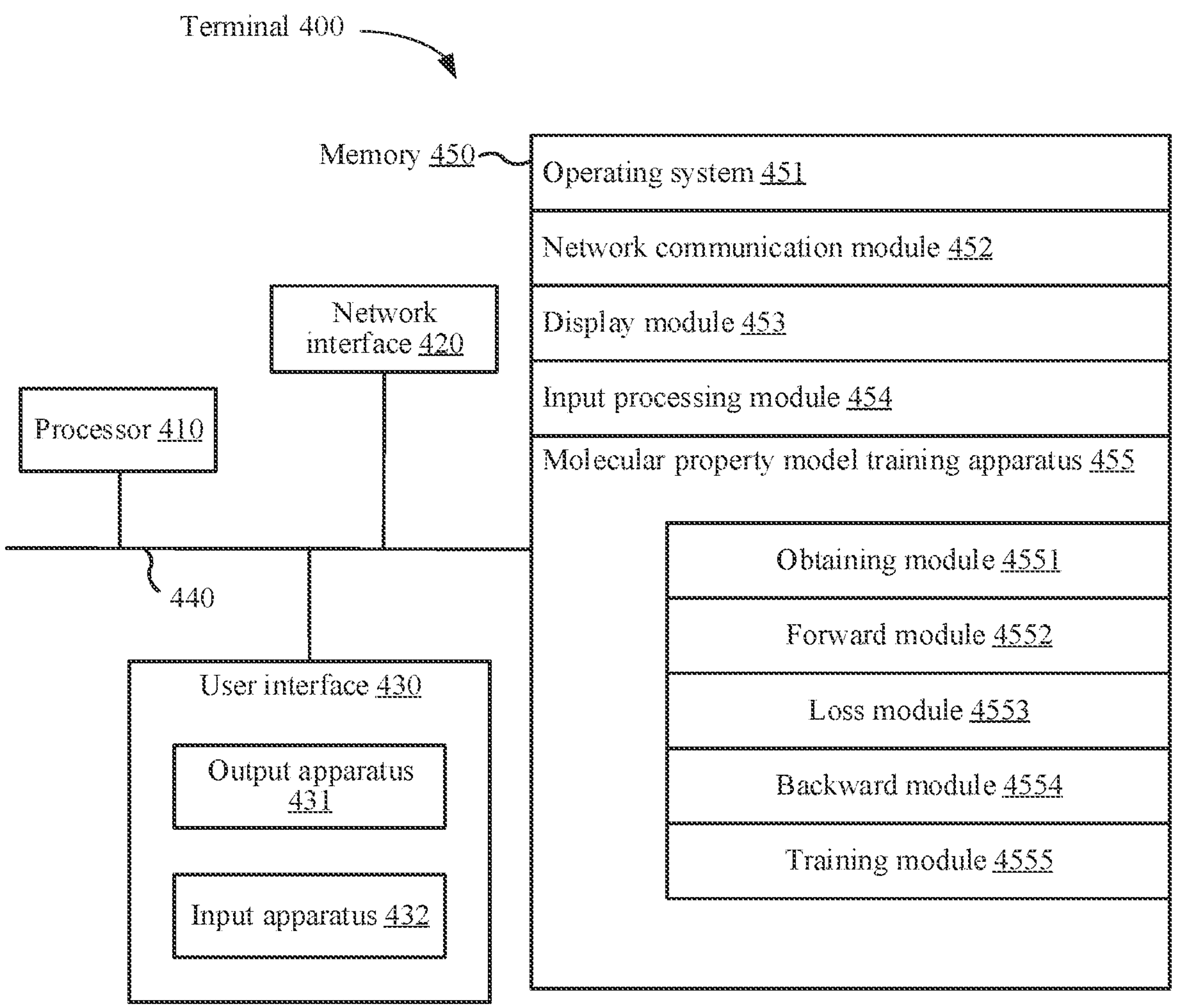
FIG. 2 is a schematic diagram of a structure of an electronic device according to an embodiment of this application.

FIG. 2 is a schematic diagram of a structure of an electronic device according to an embodiment of this application. A terminal 400 shown in FIG. 2 includes at least one processor 410, a memory 450, at least one network interface 420, and a user interface 430. Components in the terminal 400 are coupled together by a bus system 440. The bus system 440 is configured to implement connection and communication between the components. In addition to a data bus, the bus system 440 further includes a power bus, a control bus, and a status signal bus. However, for clarity, various buses are marked as the bus system 440 in FIG. 2.

The processor 410 may be an integrated circuit chip with signal processing capabilities, such as a general-purpose processor, a digital signal processor (DSP), or another programmable logic device, a discrete gate or a transistor logic device, or a discrete hardware component. The general-purpose processor may be a microprocessor, any conventional processor, or the like.

The user interface 430 includes one or more output apparatuses 431 that render a media content, including one or more loudspeakers and/or one or more visual display screens. The user interface 430 further includes one or more input apparatuses 432 including user interface members that help user input, such as a keyboard, a mouse, a microphone, a touch display screen, a camera, other input buttons and controls.

The memory 450 may be removable, non-removable, or a combination thereof. For example, a hardware device includes a solid-state memory, a hard disk drive, an optical disk drive, and the like. The memory 450 may include one or more storage devices physically away from the processor 410.

The memory 450 includes a volatile memory or a non-volatile memory, and may alternatively include both volatile and non-volatile memories. The non-volatile memory may be a read only memory (ROM), and the volatile memory may be a random access memory (RAM). The memory 450 described in the embodiment of this application is intended to include any suitable types of memories.

In some embodiments, the memory 450 can store data to support various operations. Examples of the data include a program, a module, and a data structure, or a subset or a superset thereof, which are described by using examples.

An operating system 451 includes a system program used for processing various basic system services and performing hardware-related tasks, for example, a frame layer, a core library layer, and a drive layer, and is configured to implement various basic services and process a hardware-based task.

A network communication module 452 is configured to be connected to another electronic device via one or more (wired or wireless) network interfaces 420. For example, the network interface 420 includes Bluetooth, wireless compatibility certification (Wi-Fi), a universal serial bus (USB), and the like.

A display module 453 is configured to present information by one or more output apparatuses 431 (for example, display screens and speakers) associated with the user interface 430 (for example, a user interface configured to operate a peripheral device and display content and information).

An input processing module 454 is configured to detect one or more user inputs or interactions from one of the one or more input apparatuses 432 and translate the detected inputs or interactions.

In some embodiments, a molecular property model training apparatus provided in an embodiment of this application may be implemented by software. FIG. 2 shows a molecular property model training apparatus 455 stored in the memory 450. The training apparatus may be software in a form of a program and a plug-in, and includes the following software modules: an obtaining module 4551, a forward module 4552, a loss module 4553, a backward module 4554, and a training module 4555. These modules are logical modules, and therefore may be randomly combined or further divided based on a function to be implemented. The following describes a function of each module.

Figures 3A, 3B:
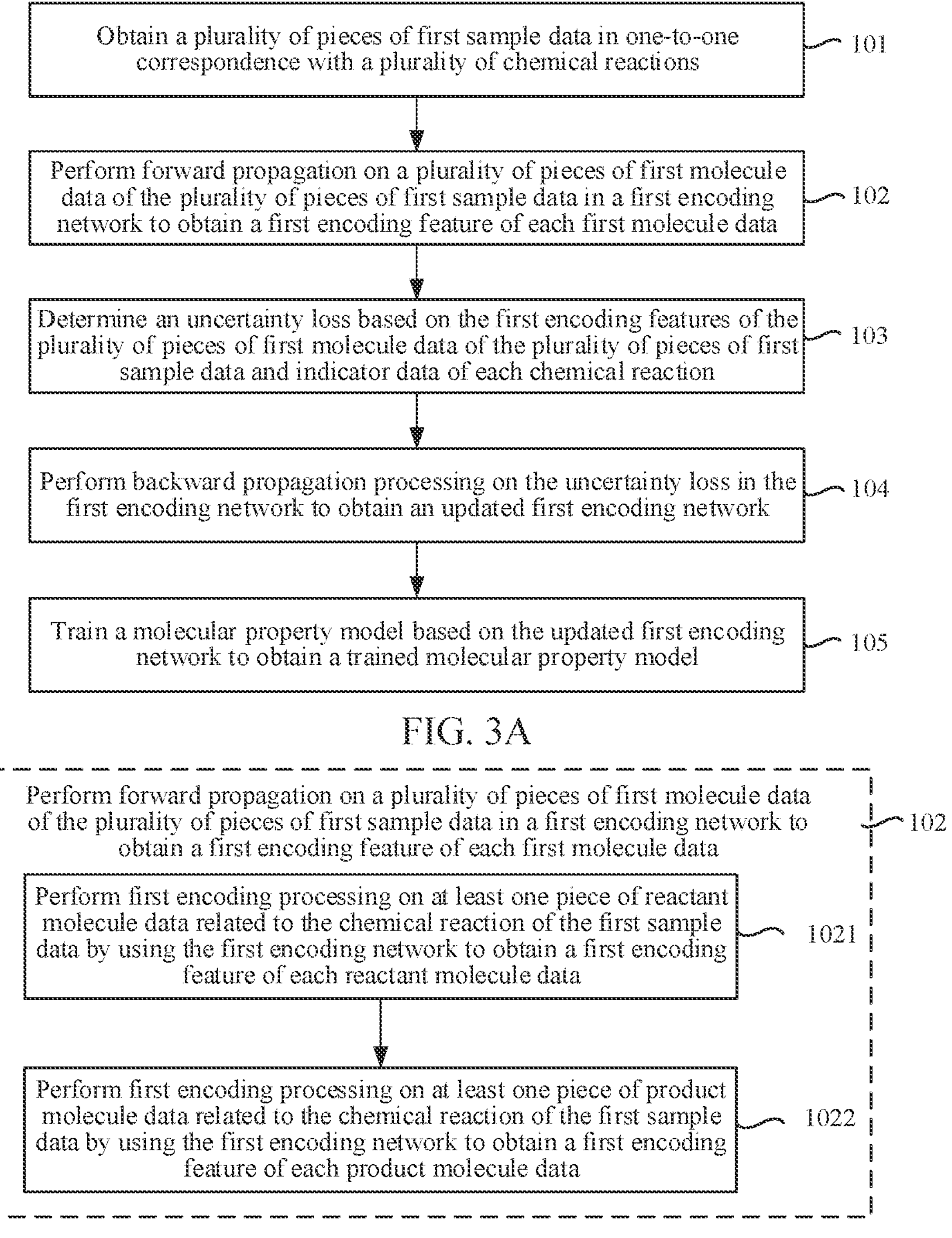
FIG. 3A to FIG. 3D are schematic flowcharts of a molecular property model training method according to an embodiment of this application.

As described above, a molecular property model training method provided in an embodiment of this application may be implemented by various types of electronic devices. The following describes the molecular property model training method provided in the embodiments of this application. As described above, an electronic device that implements the molecular property model training method provided in the embodiments of this application may be a terminal device. Therefore, an execution entity of each step is not repeatedly described below. FIG. 3A is a schematic flowchart of a molecular property model training method according to an embodiment of this application. The method is described in combination with step 101 to step 105 shown in FIG. 3A.

Step 101: Obtain a plurality of pieces of first sample data in one-to-one correspondence with a plurality of chemical reactions.

As an example, each first sample data includes a plurality of pieces of first molecule data related to a chemical reaction and indicator data of the chemical reaction. The indicator data is data representing a reaction evaluation indicator of the chemical reaction. For example, the indicator data includes a yield, an entropy change value, and the like of the chemical reaction.

As an example, for each batch of training, a plurality of pieces of first sample data in one-to-one correspondence with a plurality of chemical reactions are included. For example, there are two chemical reactions, a chemical reaction A and a chemical reaction B. For the chemical reaction A, a product PA1 and a product PA2 are obtained based on a reactant RA1 and a reactant RA2, and respective molecule graphs of the reactant RA1, the reactant RA2, the product PA1, and the product PA2 are first molecule data related to the chemical reaction A. For the chemical reaction B, a product PB1 and a product PB2 are obtained based on a reactant RB1 and a reactant RB2, and respective molecule graphs of the reactant RB1, the reactant RB2, the product PB1, and the product PB2 are first molecule data related to the chemical reaction B. V in a molecule graph G=(V,E) represents an atom set, and a set size |V| is a quantity N of atoms. Each atom $v \in V$ and is associated with an atomic feature, including a type, a charging property, an aromatic property, and the like of the atom. E represents a set of edges. Each edge $e \in E$ and is associated with a bond type, including a single bond, a double bond, a triple bond, and an aromatic bond.

Step 102: Perform forward propagation on the plurality of pieces of first molecule data of the plurality of pieces of first sample data in a first encoding network to obtain a first encoding feature of each first molecule data.

As an example, the first encoding network may be a graph neural network, such as a topology adaptive graph convolution network or a graph transformer structure. The forward propagation represents a process of performing first encoding processing by using the first encoding network.

As an example, in step 102, forward propagation is actually performed on the plurality of pieces of first molecule data of each first sample data in the first encoding network. To be specific, the first encoding processing is separately performed by using the first encoding network on the plurality of pieces of first molecule data of each first sample data in the first encoding network to obtain the first encoding feature of each first molecule data of each first sample data.

In some embodiments, the first molecule data includes reactant molecule data and product molecule data related to the corresponding chemical reactions. The chemical reaction A is used as an example for description. The reactant molecule data is respective molecule graphs of the reactant RA1 and the reactant RA2, and the product molecule data is respective molecule graphs of the product PA1 and the product PA2.

FIG. 3B is a schematic flowchart of a molecular property model training method according to an embodiment of this application. The performing forward propagation on the plurality of pieces of first molecule data of the plurality of pieces of first sample data in a first encoding network to obtain a first encoding feature of each first molecule data in step 102 may be implemented by performing step 1021 to step 1022 in FIG. 3B for each first sample data.

Step 1021: Perform first encoding processing on at least one piece of reactant molecule data related to the chemical reaction of the first sample data by using the first encoding network to obtain a first encoding feature of each reactant molecule data.

The chemical reaction A is used as an example for description. The first encoding processing is performed on the respective molecule graphs of the reactant RA1 and the reactant RA2 related to the chemical reaction A by using the first encoding network to obtain a first encoding feature of the reactant RA1 and a first encoding feature of the reactant RA2.

The first encoding processing is implemented by a graph neural network, and the graph neural network includes N cascaded network layers. A value range of N satisfies 2≤N. The performing the first encoding processing on at least one piece of reactant molecule data related to the chemical reaction of the first sample data by using the first encoding network to obtain a first encoding feature of each reactant molecule data in step 1021 may be implemented by the following technical solutions.

The following processing is performed on each reactant molecule data: obtaining an initial feature of at least one atom of the reactant molecule data; and performing, by an $n^{th}$ network layer in the N cascaded network layers, feature extraction processing on input of the $n^{th}$ network layer to obtain an $n^{th}$ feature extraction result, and transmitting the $n^{th}$ feature extraction result to an $(n+1)^{th}$ network layer to continue to perform feature extraction processing.

A value of n is an integer increasing from 1, and a value range of n satisfies 1≤n≤N−1. In a case that the value of n is 1, the input of the $n^{th}$ network layer is the initial feature of the reactant molecule data, and when the value of n is N−1, an $(n+1)^{th}$ feature extraction result outputted by the $(n+1)^{th}$ network layer is the first encoding feature of the reactant molecule data.

For example, assuming that N is 2, the following processing is performed on the reactant RA1 in the chemical reaction A. First feature extraction processing is performed on an initial feature of the reactant RA1 by using a first network layer to obtain a first feature extraction result of the reactant RA1, and the first feature extraction result is transmitted to a second network layer to continue to perform second feature extraction processing. The second feature extraction processing is performed on the first feature extraction result of the reactant RA1 by using the second network layer to obtain a second feature of the reactant RA1 (that is, the first encoding feature of the reactant RA1).

According to the embodiments of this application, the first encoding feature may be obtained in an iterative manner. This can effectively improve a feature expression capability of the first encoding feature of the reactant molecule data, thereby improving pre-training accuracy.

As an example, the performing, by an $n^{th}$ network layer in the N cascaded network layers, feature extraction processing performed on input of the $n^{th}$ network layer to obtain an $n^{th}$ feature extraction result may be implemented by the following technical solutions: obtaining an adjacency matrix corresponding to the molecule graph and a degree matrix corresponding to the molecule graph, the adjacency matrix being a matrix that represents an adjacent relationship between atoms, the degree matrix being a diagonal matrix, an element on the diagonal being a degree of each atom, and the degree of the atom representing a quantity of bonds associated with the atom; performing inverse transformation processing on the degree matrix, and performing matrix square root processing on an inverse result to obtain a transformation matrix of the degree matrix; multiplying the transformation matrix and the adjacency matrix, and multiplying a first multiplication result and the transformation matrix to obtain a normalized adjacency matrix; determining a graph transition matrix of the $n^{th}$ network layer based on a graph filter size of the $n^{th}$ network layer and the normalized adjacency matrix; and multiplying the graph transition matrix and an $(n-1)^{th}$ feature extraction result to obtain the $n^{th}$ feature extraction result.

A processing process of each network layer may refer to Formula (1):

$$X' = \sum_{k=0}^{K} \left(D^{-1/2} A D^{-1/2}\right)^k X W_k. \tag{1}$$

X is the input of the $n^{th}$ network layer, X' is the $n^{th}$ feature extraction result. A is the adjacency matrix of the molecule graph. D is the degree matrix of the molecule graph. $D^{-1/2}$ is the transformation matrix obtained by the square root processing after the inverse transformation is performed on the degree matrix. $(D^{-1/2}AD^{-1/2})$ is the normalized adjacency matrix. $W_k$ is a hyperparameter.

$$\sum_{k=0}^{K}(D^{-1/2}AD^{-1/2})^k$$

is the graph transition matrix of the $n^{th}$ network layer, and is used for representing parameters of a filter group in a current network layer. K is a quantity of filters, and sizes of the filters range from 1 to K. In a practical operational process of Formula (1), an exponent in a polynomial is usually 1.

As an example, the adjacency matrix is a data structure used for representing a graph. In chemistry, the adjacency matrix is often used for describing a relationship between atoms in a molecule. The adjacency matrix is a square matrix in which each element represents a type of a chemical bond between two atoms. If there is no chemical bond between two atoms, an element value is 0. The adjacency matrix may be used for describing a structure of a molecule, and a property and a reaction mechanism of a molecule. The degree matrix of a graph is used for describing variables connected to each node in the graph.

Step 1022: Perform first encoding processing on at least one piece of product molecule data related to the chemical reaction of the first sample data by using the first encoding network to obtain a first encoding feature of each product molecule data.

The chemical reaction A is used as an example for description. The first encoding processing is performed on the respective molecule graphs of the product PA1 and the product PA2 related to the chemical reaction A by using the first encoding network to obtain a first encoding feature of the product PA1 and a first encoding feature of the product PA2.

The first encoding processing is implemented by a graph neural network, and the graph neural network includes N cascaded network layers. A value range of N satisfies 2≤N. The performing first encoding processing on at least one piece of product molecule data related to the chemical reaction of the first sample data by using the first encoding network to obtain a first encoding feature of each product molecule data in step 1021 may be implemented by the following technical solutions.

The following processing is performed on each product molecule data: obtaining an initial feature of at least one atom of product molecule data; and performing, by an $n^{th}$ network layer in the N cascaded network layers, feature extraction processing on input of the $n^{th}$ network layer to obtain an $n^{th}$ feature extraction result, and transmitting the $n^{th}$ feature extraction result to an $(n+1)^{th}$ network layer to continue to perform feature extraction processing.

A value of n is an integer increasing from 1, and a value range of n satisfies 1≤n≤N−1. In a case that the value of n is 1, the input of the $n^{th}$ network layer is the initial feature of the product molecule data, and when the value of n is N−1, an $(n+1)^{th}$ feature extraction result outputted by the $(n+1)^{th}$ network layer is the first encoding feature of the product molecule data.

For example, assuming that N is 2, the following processing is performed on the product PA1 in the chemical reaction A. First feature extraction processing is performed on an initial feature of the product PA1 by using a first network layer to obtain a first feature extraction result of the product PA1, and the first feature extraction result is transmitted to a second network layer to continue to perform second feature extraction processing. The second feature extraction processing is performed on the first feature extraction result of the product PA1 by using the second network layer to obtain a second feature of the product PA1 (that is, the first encoding feature of the product PA1).

According to the embodiments of this application, the first encoding feature may be obtained in an iterative manner. This can effectively improve a feature expression capability of the first encoding feature of the product molecule data, thereby improving pre-training accuracy.

As an example, the performing, by an $n^{th}$ network layer in the N cascaded network layers, feature extraction processing performed on input of the $n^{th}$ network layer to obtain an $n^{th}$ feature extraction result may be implemented by the following technical solutions: obtaining an adjacency matrix corresponding to the molecule graph and a degree matrix corresponding to the molecule graph, the adjacency matrix being a matrix that represents an adjacent relationship between atoms, the degree matrix being a diagonal matrix, an element on the diagonal being a degree of each atom, and the degree of the atom representing a quantity of bonds associated with the atom; performing inverse transformation processing on the degree matrix, and performing matrix square root processing on an inverse result to obtain a transformation matrix of the degree matrix; multiplying the transformation matrix and the adjacency matrix, and multiplying a first multiplication result and the transformation matrix to obtain a normalized adjacency matrix; determining a graph transition matrix of the $n^{th}$ network layer based on a graph filter size of the $n^{th}$ network layer and the normalized adjacency matrix; and multiplying the graph transition matrix and an $(n-1)^{th}$ feature extraction result to obtain the $n^{th}$ feature extraction result.

A processing process of each network layer may refer to Formula (2):

$$X' = \sum_{k=0}^{K}(D^{-1/2}AD^{-1/2})^k XW_k. \quad (2)$$

X is the input of the $n^{th}$ network layer. X' is the $n^{th}$ feature extraction result. A is the adjacency matrix of the molecule graph. D is the degree matrix of the molecule graph. $D^{-1/2}$ is the transformation matrix obtained by the square root processing after the inverse transformation is performed on the degree matrix. $(D^{-1/2}AD^{-1/2})$ is the normalized adjacency matrix. $W_k$ is the graph transition matrix of the $n^{th}$ network layer, and is used for representing parameters of each filter in a current network layer. K is a quantity of filters, and sizes of the filters range from 1 to K. In a practical operational process of Formula (2), an exponent in a polynomial is usually 1.

Step 103: Determine an uncertainty loss of the plurality of chemical reactions based on the first encoding features of the plurality of pieces of first molecule data of the plurality of pieces of first sample data and indicator data of each chemical reaction.

As an example, the uncertainty loss is used for fitting uncertainty of establishment of the plurality of chemical reactions. The uncertainty represents a probability that a chemical reaction cannot be established (in other words, cannot be implemented) in an actual production process.

Figure 3C:
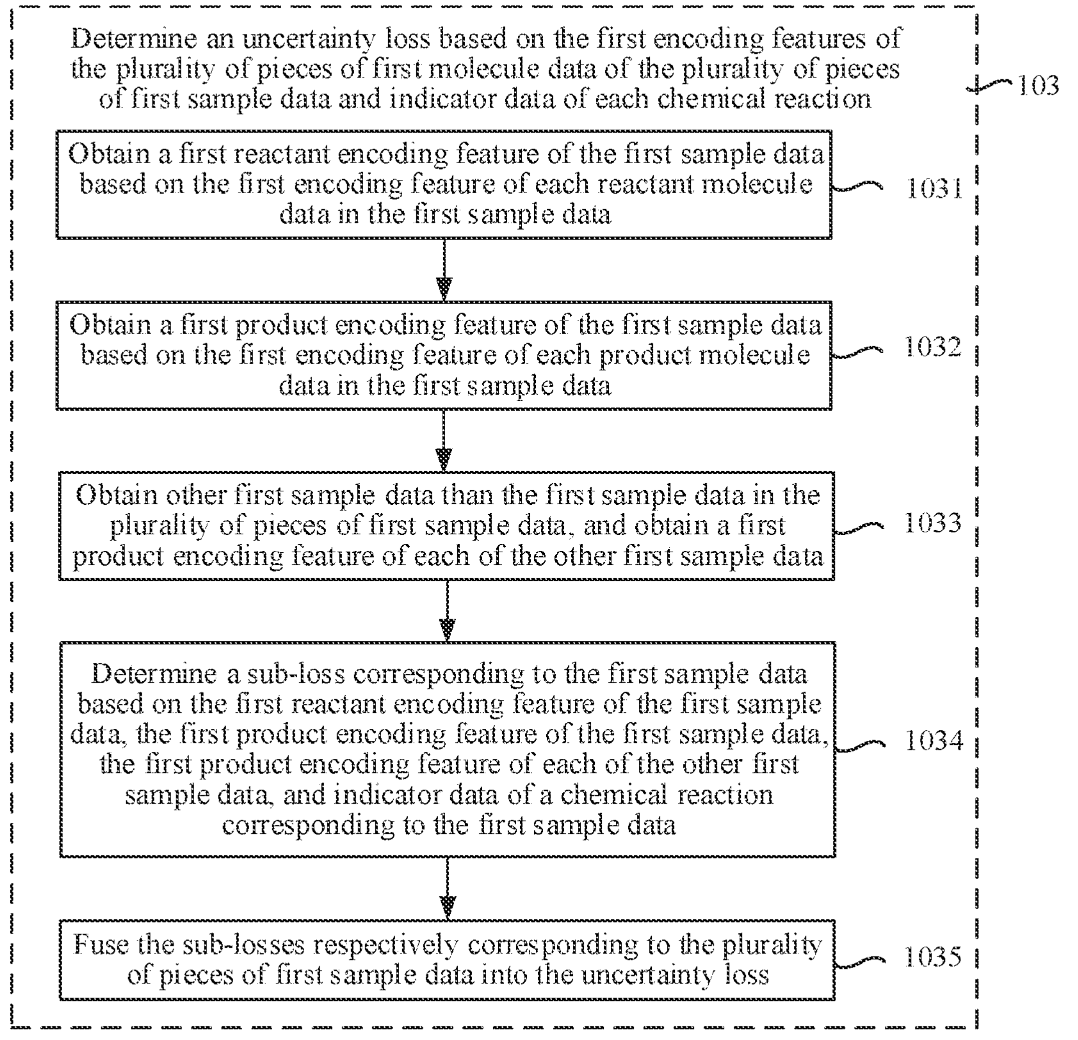

In some embodiments, the first molecule data includes the reactant molecule data and the product molecule data related to the corresponding chemical reactions. FIG. 3C is a schematic flowchart of a molecular property model training method according to an embodiment of this application. The determining an uncertainty loss of the plurality of chemical reactions based on the first encoding features of the plurality of pieces of first molecule data of the plurality of pieces of first sample data and indicator data of each chemical reaction in step 103 may be implemented by performing step 1031 to step 1034 and performing step 1035 shown in FIG. 3C for each first sample data.

Step 1031: Obtain a first reactant encoding feature of the first sample data based on the first encoding feature of each reactant molecule data in the first sample data.

In some embodiments, the obtaining a first reactant encoding feature of the first sample data based on the first encoding feature of each reactant molecule data in the first sample data in step 1031 may be implemented by the following technical solutions: when there are a plurality of pieces of reactant molecule data, fusing first encoding features of the plurality of pieces of reactant molecule data to obtain the first reactant encoding feature of the first sample data; and when there is one piece of reactant molecule data, using a first encoding feature of the reactant molecule data as the first reactant encoding feature of the first sample data.

As an example, when there are a plurality of pieces of reactant molecule data, for example, the reactant molecule data includes a molecule graph of the reactant RA1 and a molecule graph of the reactant RA2 in chemical reaction A, the first encoding feature of the reactant RA1 and the first encoding feature of the reactant RA2 are fused, such as added, to obtain the first reactant encoding feature of the first sample data. In a case that there is one piece of reactant molecule data, a first encoding feature of the reactant molecule data is used as the first reactant encoding feature of the first sample data. For example, the first encoding feature of the reactant RA1 is directly used as the first reactant encoding feature of the first sample data.

According to the embodiments of this application, all reactant encoding can be fused, to conform to entity relationship transformation of the chemical reactions, thereby facilitating fitting of the uncertainty of the plurality of chemical reactions and improving molecule encoding accuracy.

Step 1032: Obtain a first product encoding feature of the first sample data based on the first encoding feature of each product molecule data in the first sample data.

In some embodiments, the obtaining a first product encoding feature of the first sample data based on the first encoding feature of each product molecule data in the first sample data in step 1032 may be implemented by the following technical solutions: when there are a plurality of pieces of product molecule data, fusing first encoding features of the plurality of pieces of product molecule data to obtain the first product encoding feature of the first sample data; and when there is one piece of product molecule data, using a first encoding feature of the product molecule data as the first product encoding feature of the first sample data.

As an example, when there are a plurality of pieces of product molecule data, for example, the product molecule data includes a molecule graph of the product PA1 and a molecule graph of the product PA2 in chemical reaction A, the first encoding feature of the product PA1 and the first encoding feature of the product PA2 are fused, such as added, to obtain the first product encoding feature of the first sample data. In a case that there is one piece of product molecule data, a first encoding feature of the product molecule data is used as the first product encoding feature of the first sample data. For example, the first encoding feature of the product PA1 is directly used as the first product encoding feature of the first sample data.

According to the embodiments of this application, all product encoding can be fused, to conform to entity relationship transformation of the chemical reactions, thereby facilitating fitting of the uncertainty of the plurality of chemical reactions and improving molecule encoding accuracy.

Step 1033: Obtain other first sample data than the first sample data in the plurality of pieces of first sample data, and obtain a first product encoding feature of each of the other first sample data.

In some embodiments, the obtaining a first product encoding feature of each of the other first sample data in step 1033 may be implemented by the following technical solutions. The following processing is performed on each of the other first sample data: obtaining at least one of the other product molecule data including the other first sample data, and obtaining a first encoding feature of each of the other product molecule data; and fusing the first encoding features of all of the other product molecule data to obtain the first product encoding feature of the other first sample data.

As an example, in the chemical reaction A, the product PA1 and the product PA2 are obtained based on the reactant RA1 and the reactant RA1. In the chemical reaction B, the product PB1 and the product PB2 are obtained based on the reactant RB1 and the reactant RB1. For the chemical reaction A, the chemical reaction B belongs to another chemical reaction and the first molecule data related to the chemical reaction B are the other first sample data. Because there is only another chemical reaction, the chemical reaction A has one triplet. A positive sample of the triplet is second product encoding of the chemical reaction A, a negative sample of the triplet is second product encoding of the chemical reaction B, and an anchor sample of the triplet is second reactant encoding of the chemical reaction A. Because the second product encoding of the chemical reaction B needs to be obtained, a first encoding feature of the molecule graph of the product PB1 and a first encoding feature of the molecule graph of the product PB2 are obtained, and then the first encoding feature of the molecule graph of the product PB1 and the first encoding feature of the molecule graph of the product PB2 are fused to obtain a first product encoding feature of the chemical reaction B.

Because the chemical reaction A and the chemical reaction B are two different chemical reactions, the first encoding feature of the product molecule data of the chemical reaction B may be used as a negative sample of a reactant of the chemical reaction A, and the first encoding feature of the product molecule data of the chemical reaction A may be used as a negative sample of a reactant of the chemical reaction B. In this way, a negative sample does not need to be generated again, and encoding efficiency of the first encoding network can be improved.

Step 1034: Determine a sub-loss corresponding to the first sample data based on the first reactant encoding feature of the first sample data, the first product encoding feature of the first sample data, the first product encoding feature of each of the other first sample data, and indicator data of a chemical reaction corresponding to the first sample data.

In some embodiments, the determining a sub-loss corresponding to the first sample data based on the first reactant encoding feature of the first sample data, the first product encoding feature of the first sample data, the first product encoding feature of each of the other first sample data, and indicator data of a chemical reaction corresponding to the first sample data in step 1034 may be implemented by the following technical solutions:

determining a first feature distance between the first reactant encoding feature of the first sample data and the first product encoding feature of the first sample data, where the first feature distance may be a regularization result used for representing a distance between an anchor sample and a positive sample, and a smaller distance is preferred; determining a second feature distance between the first reactant encoding feature of the first sample data and the first product encoding feature of each of the other first sample data, where the second feature distance may be a regularization result used for representing a distance between an anchor sample and a negative sample, and a greater distance is preferred; and determining an uncertainty indicator in positive correlation with the indicator data of the chemical reaction corresponding to the first sample data. The indicator data may be a yield of the chemical reaction. The yield of chemical reaction measures how many products can be produced by the reactant by using the chemical reaction. A chemical reaction with a higher yield corresponds to a looser establishment condition, and indicates higher certainty (lower uncertainty) of establishment of the chemical reaction. For example, (a reactant A, generates, a product B): 0.4 represents that a score of obtaining the product B based on the reactant A is 0.4, and a higher score indicates a higher probability that an entity relationship triplet actually exists and lower uncertainty. The following processing is performed on each of the other first sample data: determining a loss value corresponding to the other first sample data based on the first feature distance, the second feature distance corresponding to the other first sample data, and the uncertainty indicator; determining the sub-loss corresponding to the first sample data based on the loss value corresponding to each of the other first sample data; and fusing the loss values corresponding to all of the other first sample data to obtain the sub-loss corresponding to the first sample data.

In some embodiments, the determining a loss value corresponding to the other first sample data based on the first feature distance, the second feature distance corresponding to the other first sample data, and the uncertainty indicator may be implemented by the following technical solutions: subtracting the second feature distance corresponding to the other first sample data by the first feature distance to obtain a first subtraction result corresponding to the other first sample data; adding the uncertainty indicator and the first subtraction result corresponding to the other first sample data to obtain a first addition result; when the first addition result is greater than zero, using the first addition result as the loss value corresponding to the other first sample data; and when the first addition result is not greater than zero, using zero as the loss value corresponding to the other first sample data.

As an example, refer to Formula (3):

$$L = \frac{1}{(|B|-1)} \sum_{i \neq j} \max\left( \left\| \sum_{r \in R_i} h_r - \sum_{p \in P_i} h_p \right\|_2 - \left\| \sum_{r \in R_i} h_r - \sum_{p \in P_j} h_p \right\|_2 + s_i^{\alpha}\gamma, 0 \right). \quad (3)$$

L is the sub-loss corresponding to the first sample data, and the first sample data corresponds to a chemical reaction i.

$$\sum_{r \in R_i} h_r$$

is the first reactant encoding feature of the first sample data.

$$\sum_{p \in P_i} h_p$$

is the first product encoding feature of the first sample data.

$$\left\| \sum_{r \in R_i} h_r - \sum_{p \in P_i} h_p \right\|_2$$

is the first feature distance.

$$\sum_{p \in P_j} h_p$$

is the first product encoding feature of the other first sample data.

$$\left\| \sum_{r \in R_i} h_r - \sum_{p \in P_j} h_p \right\|_2$$

is the second feature distance corresponding to the other first sample data.

$$s_i^{\alpha}\gamma$$

is the uncertainty indicator. $S_i$ is a yield of the chemical reaction i. B is a quantity of pieces of chemical reactions. (|B|-1) is a quantity of pieces of other first sample data. L is the sub-loss corresponding to the first sample data (corresponding to the chemical reaction i).

Step 1035: Fuse the sub-losses respectively corresponding to the plurality of pieces of first sample data into the uncertainty loss.

In some embodiments, the determining the sub-loss corresponding to the first sample data based on the loss value corresponding to each of the other first sample data in step 1035 may be implemented by the following technical solutions: when there is one piece of other first sample data, determining the loss value corresponding to the other first sample data as the sub-loss corresponding to the first sample data; and when there are a plurality of pieces of other first sample data, averaging the loss values corresponding to the plurality of pieces of other first sample data to obtain the sub-loss corresponding to the first sample data.

As an example, refer to Formula (4):

$$L = \frac{1}{|B|(|B|-1)} \sum_{i} \sum_{i \neq j} \max\left( \left\| \sum_{r \in R_i} h_r - \sum_{p \in P_i} h_p \right\|_2 - \right. \quad (4)$$

-continued $$\left\|\sum_{r\in R_i} h_r - \sum_{p\in P_j} h_p\right\|_2 + s_i^\alpha\gamma, 0\Bigg).$$

L is the uncertainty loss. B is a quantity of chemical reactions.

$$\sum_{r\in R_i} h_r$$

is the first reactant encoding feature of the first sample data.

$$\sum_{p\in P_i} h_p$$

is the first product encoding feature of the first sample data.

$$\left\|\sum_{r\in R_i} h_r - \sum_{p\in P_i} h_p\right\|_2$$

is the first feature distance.

$$\sum_{p\in P_j} h_p$$

is the first product encoding feature of the other first sample data.

$$\left\|\sum_{r\in R_i} h_r - \sum_{p\in P_j} h_p\right\|_2$$

is the second feature distance corresponding to the other first sample data.

$$s_i^\alpha\gamma$$

is the uncertainty indicator. $S_i$ is the yield of the chemical reaction i.

Step 104: Perform backward propagation processing on the uncertainty loss in the first encoding network to obtain an updated first encoding network.

As an example, the backward propagation processing is performed on the uncertainty loss in the first encoding network to obtain a parameter change value when the uncertainty loss converges. A parameter of the first encoding network is updated based on the parameter change value to obtain the updated first encoding network. The backward propagation represents to calculate a gradient of each parameter for the uncertainty loss in the first encoding network to obtain a parameter change value of the first encoding network based on the gradient of each parameter.

Step 105: Train a molecular property model based on the updated first encoding network to obtain a trained molecular property model.

Figure 3D:
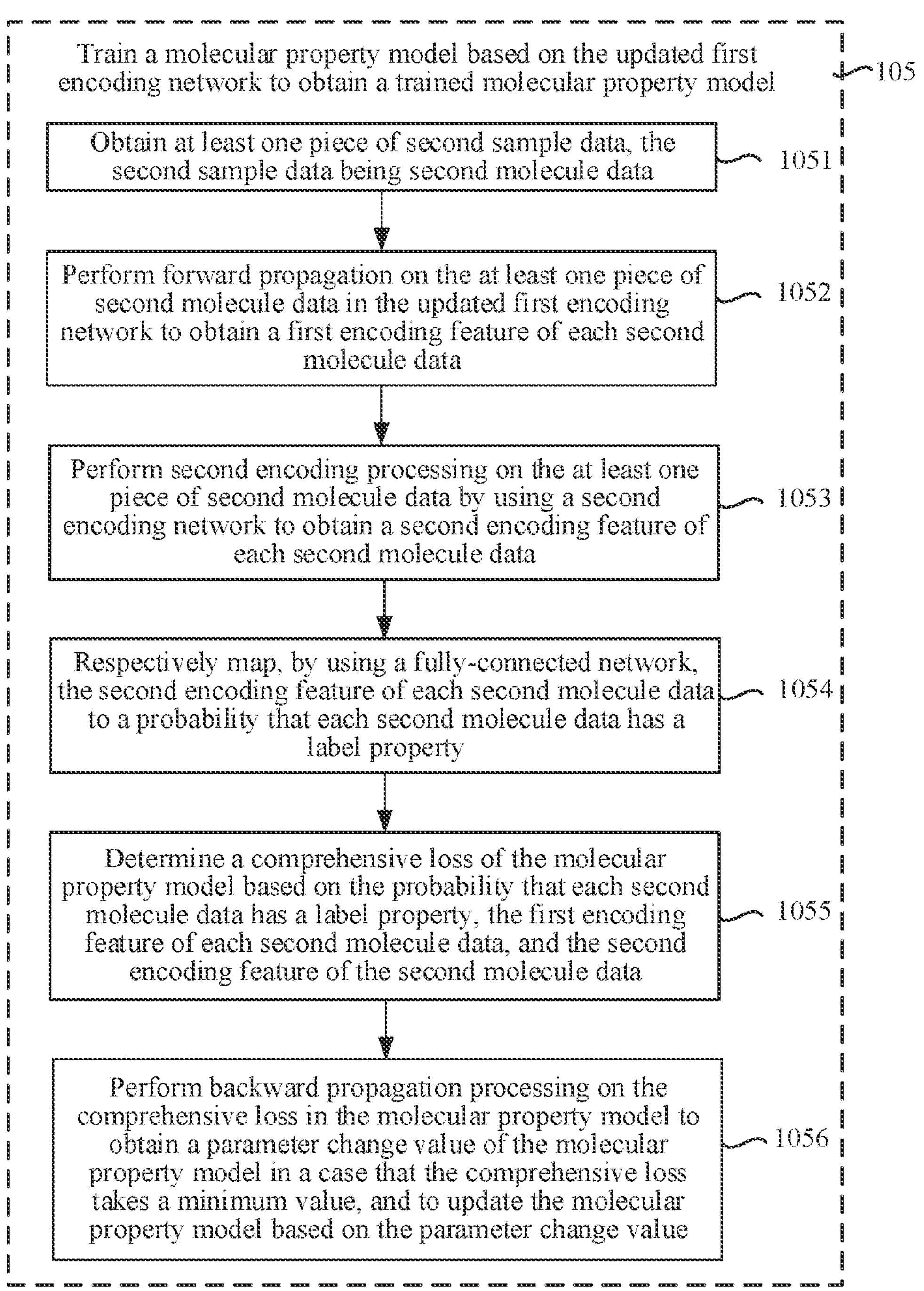

In some embodiments, the molecular property model is used for determining a property of a target molecule. The molecular property model includes a second encoding network and a fully-connected network. FIG. 3D is a schematic flowchart of a molecular property model training method according to an embodiment of this application. The training a molecular property model based on the updated first encoding network to obtain a trained molecular property model in step 105 may be implemented by step 1051 to step 1056 shown in FIG. 3D.

Step 1051: Obtain at least one piece of second sample data. The second sample data is second molecule data.

As an example, the first sample data is actually data of two ends of a chemical reaction, that is, product molecule data and reactant molecule data, and the product molecule data and the reactant molecule data depend on the chemical reaction. The second sample data is the second molecule data, and the second molecule data does not depend on any chemical reaction. In other words, the second molecule data is independent molecule data labeled with a property.

Step 1052: Perform forward propagation on the at least one piece of second molecule data in the updated first encoding network to obtain a first encoding feature of each second molecule data.

Figure 5:
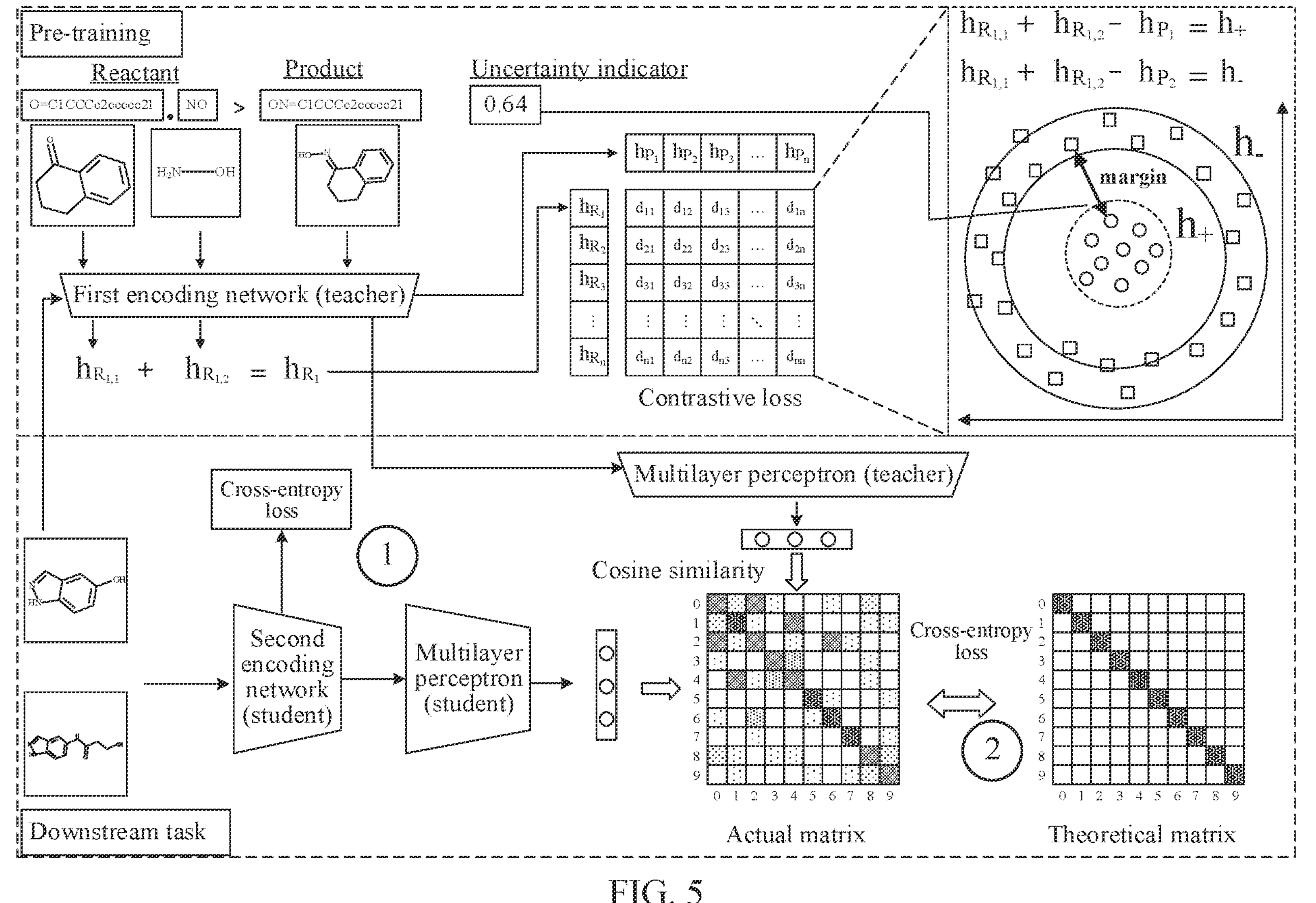
FIG. 5 is a schematic diagram of a molecular property model training architecture according to an embodiment of this application.

As an example, refer to FIG. 5. Second molecule data A is used as an example for description. The second molecule data A is a molecule graph of a specific molecule. The molecule graph is inputted into the updated first encoding network (as a teacher network) to perform the first encoding processing to obtain a first encoding feature of the second molecule data A.

Step 1053: Perform second encoding processing on the at least one piece of second molecule data by using the second encoding network to obtain a second encoding feature of each second molecule data.

As an example, refer to FIG. 5. The second molecule data A is used as an example. The second molecule data A is a molecule graph of a specific molecule. The molecule graph is inputted into the second encoding network (as a student network) to perform the second encoding processing to obtain a second encoding feature of the second molecule data A. A structure of the second encoding network here is known. For example, the second encoding network has the same network type as the first encoding network, but structural complexity of the second encoding network is usually less than that of the first encoding network. For example, the first encoding network is a graph neural network with ten network layers, but the second encoding network is a graph neural network with five network layers.

Step 1054: Respectively map, by using the fully-connected network, the second encoding feature of each second molecule data to a probability that each second molecule data has a label property.

Step 1055: Determine a comprehensive loss of the molecular property model based on the probability that each second molecule data has a label property, the second encoding feature of each second molecule data, and the first encoding feature of the second molecule data.

In some embodiments, the determining a comprehensive loss of the molecular property model based on the probability that each second molecule data has a label property, the second encoding feature of each second molecule data, and the first encoding feature of the second molecule data in step 1055 may be implemented by the following technical solutions:

performing dimension unification processing on the second encoding feature of each second molecule data and the first encoding feature of each second molecule data to obtain a first standardized encoding feature of each second molecule data and a second standardized encoding feature of each second molecule data; and performing the following processing on each second molecule data: obtaining a third feature distance between the second standardized encoding feature of the second molecule data and the first standardized encoding feature of the second molecule data.

Because the first standardized encoding feature is obtained by using the first encoding network, the first standardized encoding feature is used as the standard. The third feature distance here is used for representing a difference between encoding features obtained by encoding the same second molecule data using different encoding networks, and a smaller third feature distance is preferred. This represents that the second encoding network can achieve a similar encoding effect although the structural complexity of the second encoding network is lower than that of the first encoding network.

The following processing is performed on each second molecule data: obtaining a fourth feature distance between the second standardized encoding feature of the second molecule data and a first standardized encoding feature of each of other second molecule data.

Because the first standardized encoding feature is obtained by using the first encoding network, the first standardized encoding feature is used as the standard. The fourth feature distance here is used for representing a difference between a second standardized encoding feature of specific second molecule data and the first standardized encoding feature of the other second molecule data, and a greater difference is preferred, so that a greater fourth feature distance is preferred. This represents that the second encoding network can achieve a similar encoding effect although the structural complexity of the second encoding network is lower than that of the first encoding network.

The following processing is performed on each second molecule data: determining a knowledge distillation loss corresponding to the second molecule data based on the third feature distance and the fourth feature distance corresponding to each of the other second molecule data.

As an example, the knowledge distillation loss here may be obtained based on a cross-entropy loss function, or the triplet concept of Formula (3) may alternatively be referenced. Refer to Formula (5):

$$L=\max(D1-D2+a,0). \tag{5}$$

D1 is the third feature distance. D2 is an average value of the fourth feature distances corresponding to the plurality of pieces of other second molecule data. a is a hyperparameter. L is a knowledge distillation loss obtained based on specific second molecule data.

The following processing is performed on each second molecule data: determining a cross-entropy loss corresponding to the second molecule data based on the probability that each second molecule data has a label property and a label value corresponding to the label property, for example, a property type being flammability, when the property is flammable, the label value being 1, when the property is non-flammable, the label value being 0, and the probability and the label value being substituted into the cross-entropy loss function to obtain the cross-entropy loss; and fusing the knowledge distillation loss corresponding to the second molecule data and the cross-entropy loss corresponding to the second molecule data into a comprehensive loss corresponding to the second molecule data, and fusing the comprehensive losses corresponding to a plurality of pieces of second molecule data into the comprehensive loss of the molecular property model.

As an example, refer to Formula (6):

$$L(x,y)=\beta\cdot L_{sup}(x,y)+(1-\beta)\cdot L_{KD}(\Phi_t(f_t(x)),\Phi_s(f_s(x))). \tag{6}$$

L(x,y) is the comprehensive loss corresponding to the second molecule data A. $L_{sup}(x,y)$ is the cross-entropy loss corresponding to the second molecule data A. $L_{KD}(\Phi_t(f_t(x)), \Phi_s(f_s(x)))$ is the knowledge distillation loss. $f_t(x)$ is the first encoding feature of the second molecule data. $f_s(x)$ is the second encoding feature of the second molecule data. $\Phi_t(f_t(x))$ is the second standardized encoding feature of the second molecule data. $\Phi_s(f_s(x))$ is the first standardized encoding feature of the second molecule data. $\beta$ is an adjustment parameter.

Step 1056: Perform backward propagation processing on the comprehensive loss in the molecular property model to obtain a parameter change value of the molecular property model when the comprehensive loss takes a minimum value, and to update the molecular property model based on the parameter change value.

According to the embodiments of this application, the first encoding network is pre-trained, and then the molecular property model is trained based on a pre-trained first encoding network. In a pre-training process, the pre-training process is supervised based on a chemical reaction relationship and the indicator data of the chemical reaction, and the indicator data of the chemical reaction is used to model the uncertainty of establishment of the chemical reactions, so that a molecular representation capability of the first encoding network can be effectively improved. Therefore, the molecular property model is trained based on the first encoding network. This can effectively improve a training effect of the molecular property model, thereby improving prediction accuracy of the molecular property model.

Example application of the embodiments of this application in a practical application scenario is described below.

A terminal (on which a client, such as a compound screening client, runs) may be used to obtain a training request for a molecular property model. For example, research and development personnel input a molecular property prediction task on an input interface of the terminal, and the training request for the molecular property model is automatically generated. The terminal sends the training request for the molecular property model to a server. The server obtains a plurality of pieces of first sample data in one-to-one correspondence with a plurality of chemical reactions, where each first sample data includes a plurality of pieces of first molecule data related to a chemical reaction and indicator data of the chemical reaction; performs forward propagation on the plurality of pieces of first molecule data of the plurality of pieces of first sample data in a first encoding network to obtain a first encoding feature of each first molecule data; determines an uncertainty loss of the plurality of chemical reactions based on the first encoding features of the plurality of pieces of first molecule data of the plurality of pieces of first sample data and indicator data of each chemical reaction, and performs backward propagation processing on the uncertainty loss in the first encoding network to obtain an updated first encoding network; and trains the molecular property model based on the updated first encoding network to obtain a trained molecular property model. The server returns the molecular property model to the terminal. The research and development personnel input a target molecule on the input interface of the terminal, and the terminal predicts a property of the target molecule by calling the molecular property model. In this way, the research and development personnel can perform subsequent analysis and research based on the property of the target molecule.

In some embodiments, a molecular property prediction task is of extremely important significance to the field of computational chemistries and pharmaceuticals. In related art, molecular representations are usually determined based on a template matching method. However, there are many types of molecules, and it is difficult for molecular templates to cover a large number of molecules to be searched. In related art, a data-driven method is also used to obtain the molecular representations. However, due to limitation of sparse labeled molecule data, a training effect of a molecular property model is poor, resulting in low property prediction accuracy of the molecular property model. Therefore, it is particularly important to use a pre-training method for a molecular property prediction task. The molecular property prediction task is an important tool for drug discovery and can improve research efficiency of new drug synthesis. An efficient molecular property prediction model can reveal some scientific rules about a molecular property and provide new scientific insights and perspectives. The molecular property prediction model can further assist in molecule generation and drug screening tasks, and determine whether a generated drug molecule meets a predetermined molecular property, thereby greatly improving efficiency of new drug research and development.

In some embodiments, an organic chemical reaction includes reactants and products. Organic chemical reaction data $R_1+R_2+\ldots\rightarrow P_1+P_2+\ldots$ may be regarded as an array ($G^r$, $G^p$). $G^r$ represents a series of reactants $R_1$, $R_2$. $G^p$ represents a series of products $P_1$, $P_2$. V in a molecule graph G=(V,E) represents an atom set, and a set size |V| is a quantity N of atoms. Each atom $v\in V$ and is associated with an atomic feature, including a type, a charging property, an aromatic property, and the like of the atom. E represents a set of edges. Each edge $e\in E$ and is associated with a bond type, including a single bond, a double bond, a triple bond, and an aromatic bond.

In some embodiments, an entity and a relationship in a knowledge graph may be regarded as two matrices. An entity matrix structure is n*d, n represents a quantity of entity vectors, d represents a dimension of each entity vector, and in the matrix, each row represents an entity vector. A relationship matrix structure is r*d, r represents a quantity of relationship vectors, and d represents a dimension of each relationship vector. An ideal state of the knowledge graph model is to extract a vector respectively from the entity matrix and the relationship matrix to perform L1 or L2 operations. A result obtained is similar to another entity vector in the entity matrix, to represent a relationship of an existing triplet (h, r, t) in the knowledge graph by using word vectors. That is, the following relationship is expected to achieve. Refer to Formula (7):

$$|h+r-t|=0. \tag{7}$$

h represents an entity vector in the entity matrix. r represents a relationship vector in the relationship matrix. t represents another entity vector in the entity matrix.

Figure 4:
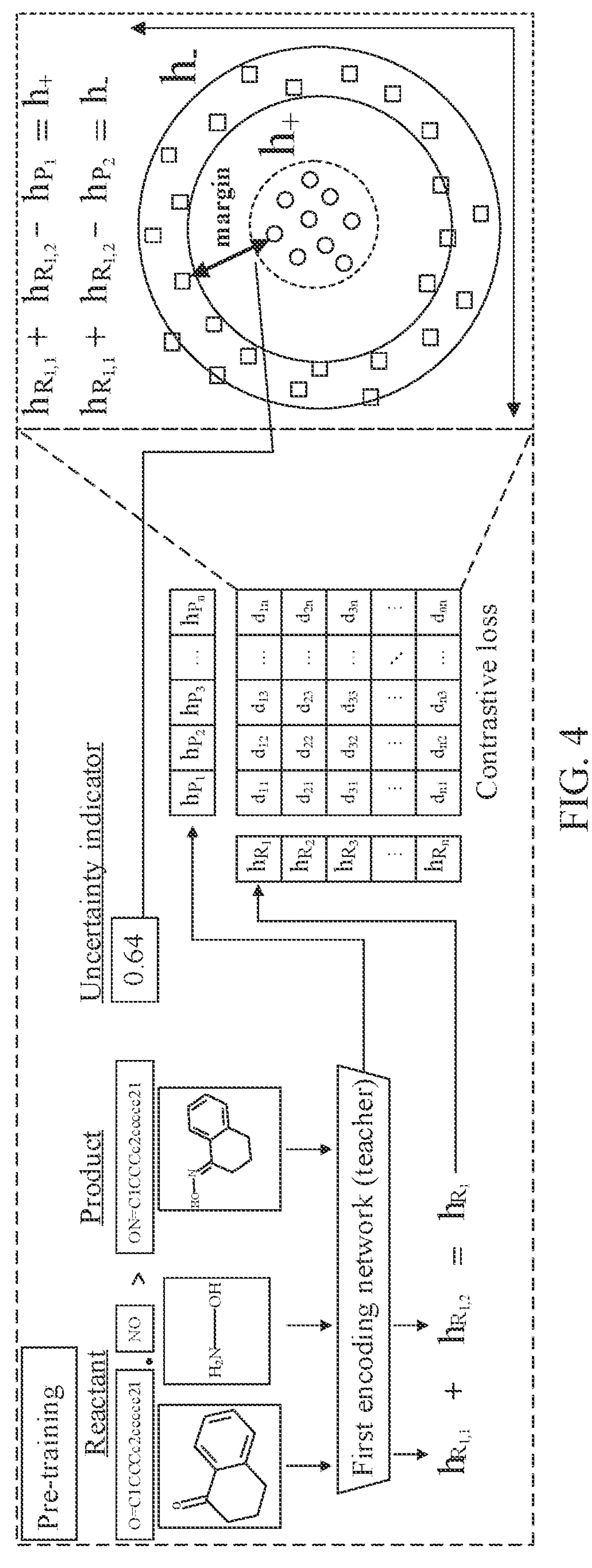
FIG. 4 is a schematic diagram of a pre-training architecture of a first encoding network according to an embodiment of this application.

Based on the foregoing knowledge graph model and molecule data (a molecule graph) related to the organic chemical reaction, a molecule pre-training algorithm based on the chemical reaction and yield information supervision is provided. FIG. 4 is a schematic diagram of a pre-training architecture of a first encoding network according to an embodiment of this application. The yield of the chemical reaction measures how many products can be produced by the reactant by using the chemical reaction. A chemical reaction with a higher yield corresponds to a looser establishment condition, and indicates higher certainty (lower uncertainty) of establishment of the chemical reaction. The yield here can correspond to the uncertainty of the entity relationship in the knowledge graph. For example, (a reactant A, generates, a product B): 0.4, represents that a score of obtaining the product B based on the reactant A is 0.4, and a higher score indicates a higher probability that an entity relationship triplet actually exists and lower uncertainty.

In the embodiment of this application, an uncertainty-based knowledge graph model is pre-trained mainly based on a triplet and an uncertainty loss, and can effectively encode a triplet with an uncertain entity relationship. For example, two chemical reactions are used as a batch for training. For a chemical reaction A, a product PA1 and a product PA2 are obtained based on a reactant RA1 and a reactant RA1. For a chemical reaction B, a product PB1 and a product PB2 are obtained based on a reactant RB1 and a reactant RB1. Two triplets may be formed. A positive sample of a first triplet is product encoding of the chemical reaction A, a negative sample of the first triplet is product encoding of the chemical reaction B, an anchor sample of the first triplet is reactant encoding of the chemical reaction A, and uncertainty is a parameter related to a yield of the chemical reaction A. A positive sample of a second triplet is product encoding of the chemical reaction B, a negative sample of the second triplet is product encoding of the chemical reaction A, an anchor sample of the second triplet is reactant encoding of the chemical reaction B, and uncertainty is a parameter related to a yield of the chemical reaction B. A loss function may refer to Formula (8):

$$L=\frac{1}{|B|(|B|-1)}\sum_i\sum_{i\neq j}\max\left(\left\|\sum_{r\in R_i}h_r-\sum_{p\in P_i}h_p\right\|_2-\left\|\sum_{r\in R_i}h_r-\sum_{p\in P_j}h_p\right\|_2+s_i^{\alpha}\gamma,0\right). \tag{8}$$

|B| represents a quantity of chemical reactions in the batch. $h_r$ is reactant encoding (representing a vector) outputted by a specific reactant by using a graph neural network. $h_p$ is product encoding (representing a vector) outputted by a specific product by using the graph neural network. $s_i$ is a yield corresponding to a chemical reaction i.

$$s_i^{\alpha}\gamma$$

is uncertainty.

In some embodiments, FIG. 5 is a schematic diagram of a training architecture of a molecular property model according to an embodiment of this application, which is mainly divided into two stages: a pre-training and a downstream prediction task. A training process is separately described below from the two stages. After completing the pre-training as in a manner shown in FIG. 4, the downstream prediction task may be trained, that is, a molecular property model may be trained. A comprehensive loss of the downstream prediction task includes two parts, a supervised loss and a knowledge distillation loss that transfers pre-trained knowledge to the downstream molecular property prediction task. Refer to Formula (9):

$$L(x, y) = \beta \cdot L_{sup}(x, y) + (1-\beta) \cdot L_{KD}(\Phi_t(f_t(x)), \Phi_s(f_s(x))). \quad (9)$$

β is an adjustment parameter controlling the supervision loss $L_{sup}$ and the knowledge distillation loss $L_{KD}$, to make the training process more stable. $\Phi_t$ and $\Phi_s$ are two multilayer perceptrons, with an object to make input feature dimensions of a feature-level knowledge distillation consistent.

A graph neural network (a first encoding network) used in the embodiment of this application is a topology-aware graph neural network model. The graph neural network model can better model a topological property of the graph. A message propagation mechanism of the graph neural network refers to Formula (10):

$$X' = \sum_{k=0}^{K} \left(D^{-1/2} A D^{-1/2}\right)^k X W_k. \quad (10)$$

A is an adjacency matrix of a molecule graph. D is a degree matrix of the molecule graph. $W_k$ is a parameter of each filter in a current layer of the graph neural network. K is a quantity of filters, and sizes of the filters range from 1 to K. The graph neural network model may be replaced by another message propagation model or a graph Transformer structure.

The training scheme provided in the embodiment of this application may perform a pre-training task based on a chemical reaction more efficiently, and use a knowledge distillation method to transfer the knowledge learned in the pre-training to the downstream molecular property prediction task.

The following continues to describe an example structure in which the molecular property model training apparatus 455 provided in the embodiments of this application is implemented as a software module. In some embodiments, as shown in FIG. 2, the software module of the molecular property model training apparatus 455 stored in the memory 450 may include: an obtaining module 4551, configured to obtain a plurality of pieces of first sample data in one-to-one correspondence with a plurality of chemical reactions, each first sample data including a plurality of pieces of first molecule data related to a chemical reactions and indicator data of the chemical reaction; a forward module 4552, configured to perform forward propagation on the plurality of pieces of first molecule data of the plurality of pieces of first sample data in a first encoding network to obtain a first encoding feature of each first molecule data; a loss module 4553, configured to determine an uncertainty loss of the plurality of chemical reactions based on the first encoding features of the plurality of pieces of first molecule data of the plurality of pieces of first sample data and indicator data of each chemical reaction, the uncertainty loss being used for fitting uncertainty of establishment of the plurality of chemical reactions; a backward module 4554, configured to perform backward propagation processing on the uncertainty loss in the first encoding network to obtain an updated first encoding network; and a training module 4555, configured to train a molecular property model based on the updated first encoding network to obtain a trained molecular property model, the molecular property model being used for determining a property of a target molecule.

In some embodiments, the first molecule data includes reactant molecule data and product molecule data related to the corresponding chemical reactions. The forward module 4552 is further configured to perform the following processing on each first sample data: performing first encoding processing on at least one piece of reactant molecule data related to the chemical reaction of the first sample data by using the first encoding network to obtain a first encoding feature of each reactant molecule data; and performing first encoding processing on at least one piece of product molecule data related to the chemical reaction of the first sample data by using the first encoding network to obtain a first encoding feature of each product molecule data.

In some embodiments, the first encoding processing is implemented by a graph neural network, and the graph neural network includes N cascaded network layers. The forward module 4552 is further configured to perform the following processing on each reactant molecule data: obtaining an initial feature of the reactant molecule data; and performing, by an $n^{th}$ network layer in the N cascaded network layers, feature extraction processing on input of the $n^{th}$ network layer to obtain an $n^{th}$ feature extraction result, and transmitting the $n^{th}$ feature extraction result to an $(n+1)^{th}$ network layer to continue to perform feature extraction processing, a value range of N satisfying $2 \leq N$, a value of n being an integer increasing from 1, and a value range of n satisfying $1 \leq n \leq N-1$; and when the value of n is 1, the input of the $n^{th}$ network layer being the initial feature of the reactant molecule data, and when the value of n is N−1, an $(n+1)^{th}$ feature extraction result outputted by the $(n+1)^{th}$ network layer being the first encoding feature of the reactant molecule data.

In some embodiments, the forward module 4552 is further configured to: obtain a molecule graph of the reactant molecule data, an adjacency matrix corresponding to the molecule graph, and a degree matrix corresponding to the molecule graph; perform inverse transformation processing on the degree matrix, and perform matrix square root processing on an inverse result to obtain a transformation matrix of the degree matrix; multiply the transformation matrix and the adjacency matrix, and multiply a first multiplication result and the transformation matrix to obtain a normalized adjacency matrix; determine a graph transition matrix of the $n^{th}$ network layer based on a graph filter size of the $n^{th}$ network layer and the normalized adjacency matrix; and multiply the graph transition matrix and an $(n-1)^{th}$ feature extraction result to obtain the $n^{th}$ feature extraction result.

In some embodiments, the first molecule data includes the reactant molecule data and the product molecule data related to the corresponding chemical reactions. The loss module 4553 is further configured to perform the following processing on each first sample data: obtaining a first reactant encoding feature of the first sample data based on the first encoding feature of each reactant molecule data in the first sample data; obtaining a first product encoding feature of the first sample data based on the first encoding feature of each product molecule data in the first sample data; obtaining other first sample data than the first sample data in the plurality of pieces of first sample data, and obtaining a first product encoding feature of each of the other first sample data; determining a sub-loss corresponding to the first sample data based on the first reactant encoding feature of the first sample data, the first product encoding feature of the first sample data, the first product encoding feature of each of the other first sample data, and indicator data of a chemical reaction corresponding to the first sample data; and fusing the sub-losses respectively corresponding to the plurality of pieces of first sample data into the uncertainty loss.

In some embodiments, the loss module 4553 is further configured to: when there are a plurality of pieces of reactant molecule data, fusing first encoding features of the plurality of pieces of reactant molecule data to obtain the first reactant encoding feature of the first sample data; and when there is one piece of reactant molecule data, using a first encoding feature of the reactant molecule data as the first reactant encoding feature of the first sample data; and when there are a plurality of pieces of product molecule data, fusing first encoding features of the plurality of pieces of product molecule data to obtain the first product encoding feature of the first sample data; and when there is one piece of product molecule data, using a first encoding feature of the product molecule data as the first product encoding feature of the first sample data.

In some embodiments, the loss module 4553 is further configured to: perform the following processing on each of the other first sample data: obtaining at least one of the other product molecule data related to the other first sample data, and obtaining a first encoding feature of each of the other product molecule data; and determining the first product encoding feature of the other first sample data based on the first encoding feature of each of the other product molecule data.

In some embodiments, the loss module 4553 is further configured to: determine a first feature distance between the first reactant encoding feature of the first sample data and the first product encoding feature of the first sample data; determine a second feature distance between the first reactant encoding feature of the first sample data and the first product encoding feature of each of the other first sample data; and determine an uncertainty indicator in positive correlation with the indicator data of the chemical reaction corresponding to the first sample data; and perform the following processing on each of the other first sample data: determining a loss value corresponding to the other first sample data based on the first feature distance, the second feature distance corresponding to the other first sample data, and the uncertainty indicator; and determining the sub-loss corresponding to the first sample data based on the loss value corresponding to each of the other first sample data.

In some embodiments, the loss module 4553 is further configured to: subtracting the second feature distance corresponding to the other first sample data by the first feature distance to obtain a first subtraction result corresponding to the other first sample data; adding the uncertainty indicator and the first subtraction result corresponding to the other first sample data to obtain a first addition result; when the first addition result is greater than zero, using the first addition result as the loss value corresponding to the other first sample data; and when the first addition result is not greater than zero, using zero as the loss value corresponding to the other first sample data.

In some embodiments, the loss module 4553 is further configured to: when there is one piece of other first sample data, determining the loss value corresponding to the other first sample data as the sub-loss corresponding to the first sample data; and when there are a plurality of pieces of other first sample data, averaging the loss values corresponding to the plurality of pieces of other first sample data to obtain the sub-loss corresponding to the first sample data.

In some embodiments, the molecular property model includes a second encoding network and a fully-connected network. The training module 4555 is further configured to: obtain at least one piece of second sample data, the second sample data being second molecule data; perform forward propagation on the at least one piece of second molecule data in the updated first encoding network to obtain a first encoding feature of each second molecule data; perform second encoding processing on the at least one piece of second molecule data by using the second encoding network to obtain a second encoding feature of each second molecule data; respectively map, by using the fully-connected network, the second encoding feature of each second molecule data to a probability that each second molecule data has a label property; determine a comprehensive loss of the molecular property model based on the probability that each second molecule data has a label property, the second encoding feature of each second molecule data, and the first encoding feature of the second molecule data; and perform backward propagation processing on the comprehensive loss in the molecular property model to obtain a parameter change value of the molecular property model when the comprehensive loss takes a minimum value, and to update the molecular property model based on the parameter change value.

In some embodiments, the training module 4555 is further configured to: perform dimension unification processing on the second encoding feature of each second molecule data and the first encoding feature of each second molecule data to obtain a first standardized encoding feature of each second molecule data and a second standardized encoding feature of each second molecule data; and perform the following processing on each second molecule data: obtaining a third feature distance between the second standardized encoding feature of the second molecule data and the first standardized encoding feature of the second molecule data, and a fourth feature distance between the second standardized encoding feature of the second molecule data and a first standardized encoding feature of each of other second molecule data; determining a knowledge distillation loss corresponding to the second molecule data based on the third feature distance and the fourth feature distance corresponding to each of the other second molecule data, and determining a cross-entropy loss corresponding to the second molecule data based on the probability that each second molecule data has a label property and a label value corresponding to the label property; and fusing the knowledge distillation loss corresponding to the second molecule data and the cross-entropy loss corresponding to the second molecule data into a comprehensive loss corresponding to the second molecule data, and fusing the comprehensive losses corresponding to a plurality of pieces of second molecule data into the comprehensive loss of the molecular property model.

An embodiment of this application provides a computer program product. The computer program product includes a computer program or computer executable instructions. The computer program or the computer executable instructions are stored in a non-transitory computer-readable storage medium. A processor of an electronic device reads the computer executable instructions from the computer-readable storage medium, and the processor executes the computer executable instructions, to cause the electronic device to execute the molecular property model training method according to the embodiments of this application.

An embodiment of this application provides a non-transitory computer-readable storage medium having computer executable instructions stored thereon. When executed by a processor, the computer executable instructions cause the processor to execute the molecular property model training method provided in the embodiments of this application, for example, the molecular property model training method shown in FIG. 3A to FIG. 3D.

In some embodiments, the computer-readable storage medium may be a memory, such as an FRAM, a ROM, a PROM, an EPROM, an EEPROM, a flash memory, a magnetic memory, a compact disc, or a CD-ROM, or may be various devices including one or any combination of the foregoing memories.

In some embodiments, the computer executable instructions may be written in the form of program, software, software module, script, or code in any form of programming language (including compilation or interpretation language, or declarative or procedural language), and the computer executable instructions may be deployed in any form, including being deployed as an independent program or being deployed as a module, component, subroutine, or other units suitable for use in a computing environment.

As an example, the computer executable instructions may, but not necessarily, correspond to a file in a file system, and may be stored as a part of the file that stores other programs or data, for example, stored in one or more scripts in a hypertext markup language (HTML) document, stored in a single file dedicated to the program under discussion, or stored in a plurality of collaborative files (for example, a file that stores one or more modules, subroutines, or code parts).

As an example, the computer executable instructions may be deployed to be executed on one electronic device or on a plurality of electronic devices located in one location, alternatively, on a plurality of electronic devices distributed in a plurality of locations and interconnected through communication networks.

In this application, the term "module" in this application refers to a computer program or part of the computer program that has a predefined function and works together with other related parts to achieve a predefined goal and may be all or partially implemented by using software, hardware (e.g., processing circuitry and/or memory configured to perform the predefined functions), or a combination thereof. Each module can be implemented using one or more processors (or processors and memory). Likewise, a processor (or processors and memory) can be used to implement one or more modules. Moreover, each module can be part of an overall module that includes the functionalities of the module. In conclusion, in the embodiments of this application, the first encoding network is pre-trained, and then the molecular property model is trained based on a pre-trained first encoding network. In a pre-training process, the pre-training process is supervised based on a chemical reaction relationship and the indicator data of the chemical reaction, and the indicator data of the chemical reaction is used to model the uncertainty of establishment of the chemical reactions, so that a molecular representation capability of the first encoding network can be effectively improved. Therefore, the molecular property model is trained based on the first encoding network. This can effectively improve a training effect of the molecular property model, thereby improving prediction accuracy of the molecular property model.

The foregoing descriptions are merely embodiments of this application and are not intended to limit the protection scope of this application. Any modification, equivalent replacement and improvement made within the spirit and scope of this application fall within the protection scope of this application.

What is claimed is:

1. A molecular property model training method executed by an electronic device, the method comprising:

obtaining a plurality of pieces of first sample data associated with a plurality of chemical reactions, each first sample data comprising a plurality of pieces of first molecule data related to a corresponding chemical reaction and indicator data of the chemical reaction;

performing forward propagation on the plurality of pieces of first molecule data of the plurality of pieces of first sample data in a first encoding network to obtain a first encoding feature of each first molecule data;

determining an uncertainty loss of the plurality of chemical reactions based on the first encoding features of the plurality of pieces of first molecule data of the plurality of pieces of first sample data and indicator data of each chemical reaction, the uncertainty loss being used for fitting uncertainty of establishment of the plurality of chemical reactions; and performing backward propagation processing on the uncertainty loss in the first encoding network to obtain an updated first encoding network as a molecular property model, the molecular property model being used for determining a property of a target molecule.

2. The method according to claim 1, wherein the first molecule data comprises reactant molecule data and product molecule data related to the corresponding chemical reactions; and the performing forward propagation on the plurality of pieces of first molecule data of the plurality of pieces of first sample data in a first encoding network to obtain a first encoding feature of each first molecule data comprises:

performing the following processing on each first sample data:

performing first encoding processing on at least one piece of reactant molecule data related to the chemical reaction of the first sample data by using the first encoding network to obtain a first encoding feature of each reactant molecule data; and performing first encoding processing on at least one piece of product molecule data related to the chemical reaction of the first sample data by using the first encoding network to obtain a first encoding feature of each product molecule data.

3. The method according to claim 2, wherein the first encoding processing is implemented by a graph neural network, and the graph neural network comprises N cascaded network layers; and the performing first encoding processing on at least one piece of reactant molecule data related to the chemical reaction of the first sample data by using the first encoding network to obtain a first encoding feature of each reactant molecule data comprises:

performing the following processing on each reactant molecule data:

obtaining an initial feature of the reactant molecule data; and performing, by an $n^{th}$ network layer in the N cascaded network layers, feature extraction processing on input of the $n^{th}$ network layer to obtain an $n^{th}$ feature extraction result, and transmitting the $n^{th}$ feature extraction result to an $(n+1)^{th}$ network layer to continue to perform feature extraction processing, a value range of N satisfying $2 \le N$, a value of n being an integer increasing from 1, and a value range of n satisfying $1 \le n \le N-1$; and when the value of n is 1, the input of the $n^{th}$ network layer being the initial feature of the reactant molecule data, and when the value of n is N−1, an $(n+1)^{h}$ feature extraction result outputted by the $(n+1)^{t}$h network layer being the first encoding feature of the reactant molecule data.

4. The method according to claim 1, wherein the first molecule data comprises the reactant molecule data and the product molecule data related to the corresponding chemical reactions, and the determining an uncertainty loss of the plurality of chemical reactions based on the first encoding features of the plurality of pieces of first molecule data of the plurality of pieces of first sample data and indicator data of each chemical reaction comprises:

performing the following processing on each selected first sample data:

obtaining a first reactant encoding feature of the first sample data based on the first encoding feature of each reactant molecule data in the first sample data;

obtaining a first product encoding feature of the first sample data based on the first encoding feature of each product molecule data in the first sample data;

obtaining other first sample data than the selected first sample data in the plurality of pieces of first sample data, and obtaining a first product encoding feature of each of the other first sample data;

determining a sub-loss corresponding to the first sample data based on the first reactant encoding feature of the first sample data, the first product encoding feature of the first sample data, the first product encoding feature of each of the other first sample data, and indicator data of a chemical reaction corresponding to the first sample data; and fusing the sub-losses respectively corresponding to the plurality of pieces of first sample data into the uncertainty loss.

5. The method according to claim 4, wherein the obtaining a first reactant encoding feature of the first sample data based on the first encoding feature of each reactant molecule data in the first sample data comprises:

when there are a plurality of pieces of reactant molecule data, fusing first encoding features of the plurality of pieces of reactant molecule data to obtain the first reactant encoding feature of the first sample data; and when there is one piece of reactant molecule data, using a first encoding feature of the reactant molecule data as the first reactant encoding feature of the first sample data; and the obtaining a first product encoding feature of the first sample data based on the first encoding feature of each product molecule data in the first sample data comprises:

when there are a plurality of pieces of product molecule data, fusing first encoding features of the plurality of pieces of product molecule data to obtain the first product encoding feature of the first sample data; and when there is one piece of product molecule data, using a first encoding feature of the product molecule data as the first product encoding feature of the first sample data.

6. The method according to claim 4, wherein the obtaining a first product encoding feature of each of the other first sample data comprises:

performing the following processing on each of the other first sample data:

obtaining at least one of the other product molecule data related to the other first sample data, and obtaining a first encoding feature of each of the other product molecule data; and fusing the first encoding features of all of the other product molecule data to obtain the first product encoding feature of the other first sample data.

7. The method according to claim 4, wherein the determining a sub-loss corresponding to the first sample data based on the first reactant encoding feature of the first sample data, the first product encoding feature of the first sample data, the first product encoding feature of each of the other first sample data, and indicator data of a chemical reaction corresponding to the first sample data comprises:

determining a first feature distance between the first reactant encoding feature of the first sample data and the first product encoding feature of the first sample data;

determining a second feature distance between the first reactant encoding feature of the first sample data and the first product encoding feature of each of the other first sample data; and determining an uncertainty indicator in positive correlation with the indicator data of the chemical reaction corresponding to the first sample data; and performing the following processing on each of the other first sample data: determining a loss value corresponding to the other first sample data based on the first feature distance, the second feature distance corresponding to the other first sample data, and the uncertainty indicator; and fusing the loss values corresponding to all of the other first sample data to obtain the sub-loss corresponding to the first sample data.

8. The method according to claim 1, wherein the molecular property model further comprises a second encoding network and a fully-connected network; and the molecular property model is trained by:

obtaining at least one piece of second sample data, the second sample data including second molecule data;

performing forward propagation on the at least one piece of second molecule data in the updated first encoding network to obtain a first encoding feature of each second molecule data;

performing second encoding processing on the at least one piece of second molecule data by using the second encoding network to obtain a second encoding feature of each second molecule data;

respectively mapping, by using the fully-connected network, the second encoding feature of each second molecule data to a probability that each second molecule data has a label property;

determining a comprehensive loss of the molecular property model based on the probability that each second molecule data has a label property, the second encoding feature of each second molecule data, and the first encoding feature of the second molecule data; and performing backward propagation processing on the comprehensive loss in the molecular property model to obtain a parameter change value of the molecular property model when the comprehensive loss takes a minimum value, and to update the molecular property model based on the parameter change value.

9. The method according to claim 1, wherein the uncertainty represents a probability that a chemical reaction cannot be implemented in an actual production process.

10. An electronic device, comprising:

a memory, configured to store executable instructions; and a processor, configured to execute the executable instructions stored in the memory to implement a molecular property model training method including:

obtaining a plurality of pieces of first sample data associated with a plurality of chemical reactions, each first sample data comprising a plurality of pieces of first molecule data related to a corresponding chemical reaction and indicator data of the chemical reaction;

performing forward propagation on the plurality of pieces of first molecule data of the plurality of pieces of first sample data in a first encoding network to obtain a first encoding feature of each first molecule data;

determining an uncertainty loss of the plurality of chemical reactions based on the first encoding features of the plurality of pieces of first molecule data of the plurality of pieces of first sample data and indicator data of each chemical reaction, the uncertainty loss being used for fitting uncertainty of establishment of the plurality of chemical reactions; and performing backward propagation processing on the uncertainty loss in the first encoding network to obtain an updated first encoding network as a molecular property model, the molecular property model being used for determining a property of a target molecule.

11. The electronic device according to claim 10, wherein the first molecule data comprises reactant molecule data and product molecule data related to the corresponding chemical reactions; and the performing forward propagation on the plurality of pieces of first molecule data of the plurality of pieces of first sample data in a first encoding network to obtain a first encoding feature of each first molecule data comprises:

performing the following processing on each first sample data:

performing first encoding processing on at least one piece of reactant molecule data related to the chemical reaction of the first sample data by using the first encoding network to obtain a first encoding feature of each reactant molecule data; and performing first encoding processing on at least one piece of product molecule data related to the chemical reaction of the first sample data by using the first encoding network to obtain a first encoding feature of each product molecule data.

12. The electronic device according to claim 11, wherein the first encoding processing is implemented by a graph neural network, and the graph neural network comprises N cascaded network layers; and the performing first encoding processing on at least one piece of reactant molecule data related to the chemical reaction of the first sample data by using the first encoding network to obtain a first encoding feature of each reactant molecule data comprises:

performing the following processing on each reactant molecule data:

obtaining an initial feature of the reactant molecule data; and performing, by an $n^{th}$ network layer in the N cascaded network layers, feature extraction processing on input of the $n^{th}$ network layer to obtain an $n^{th}$ feature extraction result, and transmitting the $n^{th}$ feature extraction result to an $(n+1)^{th}$ network layer to continue to perform feature extraction processing, a value range of N satisfying $2 \le N$, a value of n being an integer increasing from 1, and a value range of n satisfying $1 \le n \le N-1$; and when the value of n is 1, the input of the $n^{th}$ network layer being the initial feature of the reactant molecule data, and when the value of n is $N-1$, an $(n+1)^{th}$ feature extraction result outputted by the $(n+1)^{th}$ network layer being the first encoding feature of the reactant molecule data.

13. The electronic device according to claim 10, wherein the first molecule data comprises the reactant molecule data and the product molecule data related to the corresponding chemical reactions, and the determining an uncertainty loss of the plurality of chemical reactions based on the first encoding features of the plurality of pieces of first molecule data of the plurality of pieces of first sample data and indicator data of each chemical reaction comprises:

performing the following processing on each selected first sample data:

obtaining a first reactant encoding feature of the first sample data based on the first encoding feature of each reactant molecule data in the first sample data;

obtaining a first product encoding feature of the first sample data based on the first encoding feature of each product molecule data in the first sample data;

obtaining other first sample data than the selected first sample data in the plurality of pieces of first sample data, and obtaining a first product encoding feature of each of the other first sample data;

determining a sub-loss corresponding to the first sample data based on the first reactant encoding feature of the first sample data, the first product encoding feature of the first sample data, the first product encoding feature of each of the other first sample data, and indicator data of a chemical reaction corresponding to the first sample data; and fusing the sub-losses respectively corresponding to the plurality of pieces of first sample data into the uncertainty loss.

14. The electronic device according to claim 13, wherein the obtaining a first reactant encoding feature of the first sample data based on the first encoding feature of each reactant molecule data in the first sample data comprises:

when there are a plurality of pieces of reactant molecule data, fusing first encoding features of the plurality of pieces of reactant molecule data to obtain the first reactant encoding feature of the first sample data; and when there is one piece of reactant molecule data, using a first encoding feature of the reactant molecule data as the first reactant encoding feature of the first sample data; and the obtaining a first product encoding feature of the first sample data based on the first encoding feature of each product molecule data in the first sample data comprises:

when there are a plurality of pieces of product molecule data, fusing first encoding features of the plurality of pieces of product molecule data to obtain the first product encoding feature of the first sample data; and when there is one piece of product molecule data, using a first encoding feature of the product molecule data as the first product encoding feature of the first sample data.

15. The electronic device according to claim 13, wherein the obtaining a first product encoding feature of each of the other first sample data comprises:

performing the following processing on each of the other first sample data:

obtaining at least one of the other product molecule data related to the other first sample data, and obtaining a first encoding feature of each of the other product molecule data; and fusing the first encoding features of all of the other product molecule data to obtain the first product encoding feature of the other first sample data.

16. The electronic device according to claim 13, wherein the determining a sub-loss corresponding to the first sample data based on the first reactant encoding feature of the first sample data, the first product encoding feature of the first sample data, the first product encoding feature of each of the other first sample data, and indicator data of a chemical reaction corresponding to the first sample data comprises:

determining a first feature distance between the first reactant encoding feature of the first sample data and the first product encoding feature of the first sample data;

determining a second feature distance between the first reactant encoding feature of the first sample data and the first product encoding feature of each of the other first sample data; and determining an uncertainty indicator in positive correlation with the indicator data of the chemical reaction corresponding to the first sample data; and performing the following processing on each of the other first sample data: determining a loss value corresponding to the other first sample data based on the first feature distance, the second feature distance corresponding to the other first sample data, and the uncertainty indicator; and fusing the loss values corresponding to all of the other first sample data to obtain the sub-loss corresponding to the first sample data.

17. The electronic device according to claim 10, wherein the molecular property model further comprises a second encoding network and a fully-connected network; and the molecular property model is trained by:

obtaining at least one piece of second sample data, the second sample data including second molecule data;

performing forward propagation on the at least one piece of second molecule data in the updated first encoding network to obtain a first encoding feature of each second molecule data;

performing second encoding processing on the at least one piece of second molecule data by using the second encoding network to obtain a second encoding feature of each second molecule data;

respectively mapping, by using the fully-connected network, the second encoding feature of each second molecule data to a probability that each second molecule data has a label property;

determining a comprehensive loss of the molecular property model based on the probability that each second molecule data has a label property, the second encoding feature of each second molecule data, and the first encoding feature of the second molecule data; and performing backward propagation processing on the comprehensive loss in the molecular property model to obtain a parameter change value of the molecular property model when the comprehensive loss takes a minimum value, and to update the molecular property model based on the parameter change value.

18. The electronic device according to claim 10, wherein the uncertainty represents a probability that a chemical reaction cannot be implemented in an actual production process.

19. A non-transitory computer-readable storage medium, having computer executable instructions stored thereon, the computer executable instructions, when executed by a processor of an electronic device, causing the electronic device to implement a molecular property model training method including:

obtaining a plurality of pieces of first sample data associated with a plurality of chemical reactions, each first sample data comprising a plurality of pieces of first molecule data related to a corresponding chemical reaction and indicator data of the chemical reaction;

performing forward propagation on the plurality of pieces of first molecule data of the plurality of pieces of first sample data in a first encoding network to obtain a first encoding feature of each first molecule data;

determining an uncertainty loss of the plurality of chemical reactions based on the first encoding features of the plurality of pieces of first molecule data of the plurality of pieces of first sample data and indicator data of each chemical reaction, the uncertainty loss being used for fitting uncertainty of establishment of the plurality of chemical reactions; and performing backward propagation processing on the uncertainty loss in the first encoding network to obtain an updated first encoding network as a molecular property model, the molecular property model being used for determining a property of a target molecule.

20. The non-transitory computer-readable storage medium according to claim 19, wherein the uncertainty represents a probability that a chemical reaction cannot be implemented in an actual production process.

* * * * *